United States Patent
Kondoh

(10) Patent No.: US 10,574,160 B2
(45) Date of Patent: Feb. 25, 2020

(54) CIRCUIT FOR DETECTING ROTATION ANGLE, METHOD FOR DETECTING ROTATION ANGLE, SAMPLE ANALYSIS DEVICE, AND COMPUTER PROGRAM FOR SAMPLE ANALYSIS DEVICE

(71) Applicant: PHC HOLDINGS CORPORATION, Tokyo (JP)

(72) Inventor: Kazuya Kondoh, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 0 days.

(21) Appl. No.: 15/322,885

(22) PCT Filed: Jun. 29, 2015

(86) PCT No.: PCT/JP2015/068730
§ 371 (c)(1),
(2) Date: Dec. 29, 2016

(87) PCT Pub. No.: WO2016/002732
PCT Pub. Date: Jan. 7, 2016

(65) Prior Publication Data
US 2017/0141708 A1  May 18, 2017

(30) Foreign Application Priority Data
Jun. 30, 2014 (JP) ................. 2014-134775

(51) Int. Cl.
*G01P 3/48* (2006.01)
*H02P 6/16* (2016.01)
(Continued)

(52) U.S. Cl.
CPC ............. *H02P 6/16* (2013.01); *G01D 5/145* (2013.01); *G01N 21/59* (2013.01); *G01N 21/645* (2013.01);
(Continued)

(58) Field of Classification Search
CPC .. G01D 5/145; H02K 11/215; H02P 2203/03; H02P 6/16
See application file for complete search history.

(56) References Cited

U.S. PATENT DOCUMENTS

| 4,460,856 A | * | 7/1984 | Mizumoto | ............... H02P 6/08 318/400.04 |
| 2005/0242802 A1 | * | 11/2005 | Matsumoto | ............ G01D 5/145 324/174 |

(Continued)

FOREIGN PATENT DOCUMENTS

| JP | H07-500910 A | 1/1995 |
| JP | H09-154250 A | 6/1997 |

(Continued)

OTHER PUBLICATIONS

International Search Report issued in Application No. PCT/JP2015/068730 dated Oct. 6, 2015, with English translation.

*Primary Examiner* — Muhammad S Islam
(74) *Attorney, Agent, or Firm* — McDermott Will & Emery LLP

(57) ABSTRACT

A brushless motor includes: a 2n-pole (n: natural number) rotor; and a first Hall element and a second Hall element arranged at a positional relationship of an angle α (0°<α<180°) from each other with respect to a rotation axis of the rotor. The first Hall element and the second Hall element each output a voltage signal in accordance with a magnitude of a magnetic field of the rotor. A rotational angle detection circuit for detecting a rotational angle of the brushless motor includes: a phase detection circuit that receives the voltage signals from the first Hall element and the second Hall element and that detects a phase of the rotor by using values of the voltage signals and information of the angle α; and an angle calculation circuit that calculates a (Continued)

rotational angle of the rotor calculated from an initial angle based on the phase and a predetermined reference angle.

18 Claims, 27 Drawing Sheets

(51) Int. Cl.
*H02K 11/215* (2016.01)
*G01D 5/14* (2006.01)
*G01N 21/59* (2006.01)
*G01N 21/64* (2006.01)
*G01N 21/76* (2006.01)
*G01N 35/00* (2006.01)
*B01L 3/00* (2006.01)

(52) U.S. Cl.
CPC ....... *G01N 21/76* (2013.01); *G01N 35/00069* (2013.01); *H02K 11/215* (2016.01); *B01L 3/50273* (2013.01); *G01N 2035/00524* (2013.01); *G01N 2201/0415* (2013.01); *H02P 2203/03* (2013.01)

(56) References Cited

U.S. PATENT DOCUMENTS

| | | | |
|---|---|---|---|
| 2007/0188165 A1 | 8/2007 | Kitanaka et al. | |
| 2010/0309487 A1 | 12/2010 | Hyoudou et al. | |
| 2012/0143563 A1* | 6/2012 | Ueda | G01D 5/24476 702/151 |
| 2013/0099708 A1* | 4/2013 | Shimizu | H02P 21/146 318/400.39 |
| 2014/0347040 A1* | 11/2014 | Kawase | G01D 5/145 324/207.12 |

FOREIGN PATENT DOCUMENTS

| | | |
|---|---|---|
| JP | 2003-254780 A | 9/2003 |
| JP | 2003-315093 A | 11/2003 |
| JP | 2007-218592 A | 8/2007 |
| JP | 2009-058353 A | 3/2009 |
| JP | 2009-198489 A | 9/2009 |
| JP | 2011-069815 A | 4/2011 |
| WO | 93/008893 A1 | 5/1993 |

* cited by examiner

CIRCUIT FOR DETECTING ROTATION ANGLE, METHOD FOR DETECTING ROTATION ANGLE, SAMPLE ANALYSIS DEVICE, AND COMPUTER PROGRAM FOR SAMPLE ANALYSIS DEVICE

RELATED APPLICATIONS

This application is the U.S. National Phase under 35 U.S.C. § 371 of International Application No. PCT/JP2015/068730, filed on Jun. 29, 2015, which in turn claims the benefit of Japanese Application No. 2014-134775, filed on Jun. 30, 2014, the disclosures of which are incorporated by reference herein.

TECHNICAL FIELD

The present application relates to a rotational angle detection circuit, a rotational angle detection method, a sample analysis device and a computer program for a sample analysis device.

BACKGROUND ART

Patent Document No. 1 discloses a technique for analyzing a particular component contained in an analyte (sample) such as urine or blood. The technique disclosed in Patent Document No. 1 analyzes a particular component in an analyte by rotating a disc-shaped substrate for sample analysis having channels, chambers, etc., formed therein, so as to transfer, distribute and mix the liquid (including the analyte) having been introduced into the substrate.

Patent Document No. 2 discloses a technique, for use with the technique of Patent Document No. 1, for stopping the substrate for sample analysis at a predetermined rotational angle (position).

CITATION LIST

Patent Literature

[Patent Document No. 1]. Japanese National Phase PCT Laid-Open Publication No. 7-500910
[Patent Document No. 2] Japanese Laid-Open Patent Publication No. 09-154250

SUMMARY OF INVENTION

Technical Problem

With the technique described above, it is necessary to stop the substrate for sample analysis at a predetermined rotational angle (i.e., a position). Therefore, there has been a demand for a technique for detecting the rotational angle (position) with a higher precision.

A non-limiting example embodiment of the present application provides a technique for detecting the rotational angle (position) with a higher precision for stopping the substrate for sample analysis.

Solution to Problem

A rotational angle detection circuit according to one embodiment of the present application detects a rotational angle of a brushless motor. The brushless motor includes: a 2n-pole (n: an integer of 1 or more) rotor; and a first Hall element and a second Hall element arranged at a positional relationship of an angle α (0°<α<180°) from each other with respect to a rotation axis of the rotor, the first Hall element and the second Hall element each outputting a voltage signal in accordance with a magnitude of a magnetic field of the rotor. The rotational angle detection circuit includes: a phase detection circuit that receives the voltage signals output respectively from the first Hall element and the second Hall element and that detects a phase of the rotor by using values of the voltage signals and information of the angle α; and an angle calculation circuit to calculate a rotational angle of the rotor calculated from an initial angle of the rotor based on the phase detected by the phase detection circuit and a predetermined reference angle.

Advantageous Effects of Invention

With a rotational angle detection circuit, a rotational angle detection method, a sample analysis device and a computer program for a sample analysis device according to one embodiment of the present application, when a substrate for sample analysis is stopped, it is possible to detect the rotational angle (position) thereof with a higher precision.

DESCRIPTION OF EMBODIMENTS

Figure 1:
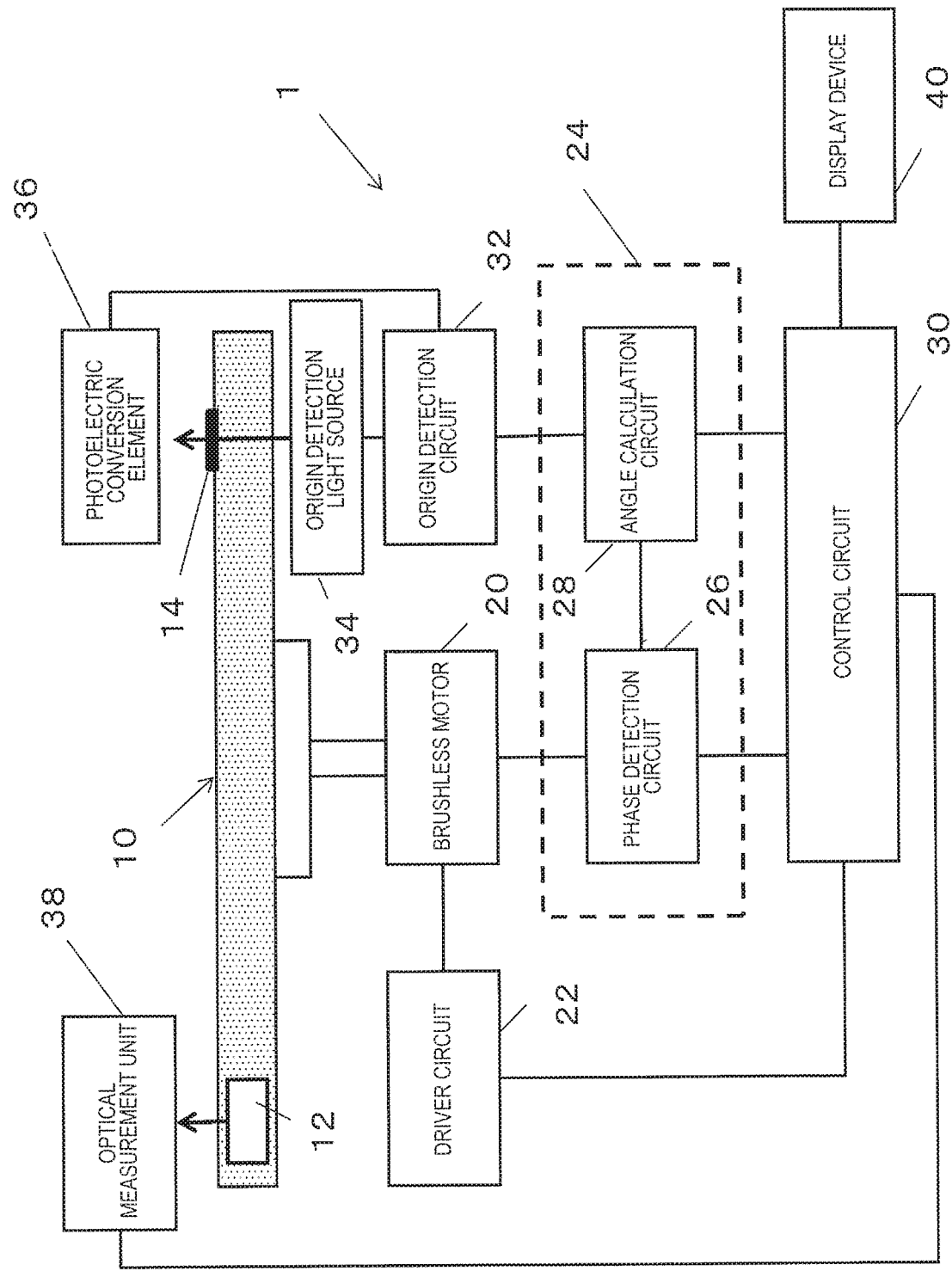
FIG. 1 A diagram showing an example configuration of a sample analysis device 1 according to an embodiment.

The present inventors made an in-depth study on the conventional configuration described above. As a result, it was found that depending on the analyzing method used, the substrate for sample analysis being rotated needs to be stopped at a predetermined rotational angle (position) with an even higher precision than those realized by conventional techniques.

Known sample analyzing methods include those using detection of light emission, such as chemiluminescence, bioluminescence and electrochemiluminescence, for example, and those using detection of fluorescent emission. In order to detect light emission or fluorescent emission, slight amounts of light need to be detected by a detector, and there should not be variations in detection precision. Therefore, the substrate for sample analysis needs to be stopped precisely at a position or rotational angle for light detection. Also, in order to realize an analysis with a higher precision using a smaller reaction field, the substrate for sample analysis needs to be stopped at an accurate position or rotational angle.

Note that there are cases where the rotational angle (position) of the substrate for sample analysis can be optically detected with a good precision using an encoder. However, there are also cases where it is not preferable to use an encoder for detecting light emission or fluorescent emission. An encoder is a device including a light source, a phototransistor, and a disc arranged therebetween with a slit provided in the disc. An encoder detects the rotational angle, or the like, of the disc by receiving, by means of the phototransistor, light that has passed through the slit as the disc rotates. As an encoder requires a light source as described above, the detector may not be able to accurately detect weak light emission or fluorescent emission due to influence of light from the light source. The detector needs to be shaded strictly in order to prevent light from the encoder from reaching the detector. We found that, as a result of this, it is necessary to provide a strict light-blocking structure for the detector, in addition to the weight of the encoder mechanism itself, thereby increasing the size of, and complicating, the sample analysis device.

The present inventors made an in-depth study on the problems set forth above, arriving at a technique with which it is possible to precisely detect the rotational angle (position) of the substrate for sample analysis, and which is suitable for reducing the size of, and/or simplifying, the sample analysis device. Rotational angle detection circuits, angle detection methods, sample analysis devices and computer programs for a sample analysis device according to one embodiment of the present application are listed below.

[Item 1] A rotational angle detection circuit for detecting a rotational angle of a brushless motor, wherein:

the brushless motor includes:

a 2n-pole (n: an integer of 1 or more) rotor; and a first Hall element and a second Hall element arranged at a positional relationship of an angle α (0°<α<180°) from each other with respect to a rotation axis of the rotor, the first Hall element and the second Hall element each outputting a voltage signal in accordance with a magnitude of a magnetic field of the rotor, the rotational angle detection circuit including:

a phase detection circuit that receives the voltage signals output respectively from the first Hall element and the second Hall element and that detects a phase of the rotor by using values of the voltage signals and information of the angle α; and an angle calculation circuit that calculates a rotational angle of the rotor calculated from an initial angle of the rotor based on the phase detected by the phase detection circuit and a predetermined reference angle.

[Item 2] The rotational angle detection circuit according to item 1, wherein:

at a first point in time, the phase detection circuit detects a first phase of the rotor; and the angle calculation circuit calculates a first rotational angle of the rotor from the initial angle of the rotor based on the first phase and the predetermined reference angle, and further updates the predetermined reference angle to the first phase;

at a second point in time different from the first point in time, the phase detection circuit detects a second phase of the rotor; and the angle calculation circuit calculates a rotational angle of the rotor from the predetermined reference angle based on the first rotational angle, the second phase and the updated predetermined reference angle.

[Item 3] The rotational angle detection circuit according to item 1, wherein an initial value of the predetermined reference angle is 0°.

[Item 4] The rotational angle detection circuit according to item 2, wherein:

when the rotor has 2n-pole (n: an integer of 2 or more), the angle calculation circuit receives, as an initial value of the predetermined reference angle, information for determining the initial angle of the rotor.

[Item 5] The rotational angle detection circuit according to item 2, wherein:

when the rotor has 2n-pole (n=1), the angle calculation circuit calculates a second rotational angle calculated from the initial angle of the rotor by adding together a difference value between the second phase and the updated predetermined reference angle and the first rotational angle.

[Item 6] The rotational angle detection circuit according to item 2, wherein:

when the rotor has 2n-pole (n: an integer of 2 or more), the angle calculation circuit calculates a second rotational angle calculated from the initial angle of the rotor by adding together a value, which is obtained by dividing by n a difference value between the second phase and the updated predetermined reference angle, and the first rotational angle.

[Item 7] The rotational angle detection circuit according to item 1, wherein the phase detection circuit detects a phase of the rotor by using the voltage signals or non-rectangular wave signals obtained from the voltage signals.

[Item 8] The rotational angle detection circuit according to item 7, wherein the phase detection circuit detects a phase of the rotor by using a ratio between values of the voltage signals and information of the angle $\alpha$.

[Item 9] The rotational angle detection circuit according to item 7, wherein:

when the voltage signal of the first Hall element is denoted as $H1 = A \sin \omega t$ and the voltage signal of the second Hall element is denoted as $H2 = A \sin(\omega t + \alpha)$, or when the voltage signal of the first Hall element is denoted as $H1 = f(t) A \sin \omega t$ and the voltage signal of the second Hall element is denoted as $H2 = f(t) A \sin(\omega t + \alpha)$, and a function $f(t)$ is a noise component which is commonly superimposed on the first Hall element and the second Hall element, the phase detection circuit detects a phase $\theta$ of the rotor by calculating:

$$\theta = \tan^{-1}(H1 \cdot \sin \alpha)/(H2 - H1 \cdot \cos \alpha).$$

[Item 10] The rotational angle detection circuit according to item 7, wherein:

when sensitivities of the first Hall element and the second Hall element are different from each other for a magnetic field of the same magnitude, and a sensitivity ratio therebetween is denoted as $\beta$, the phase detection circuit detects a phase of the rotor by using the sensitivity ratio $\beta$, a ratio between values of the voltage signals and information of the angle $\alpha$.

[Item 11] The rotational angle detection circuit according to item 9, wherein:

when the voltage signal of the first Hall element is denoted as $H1 = f(t) A \sin \omega t$ and the voltage signal of the second Hall element is denoted as $H2 = \beta f(t) A \sin(\omega t + \alpha)$, and a function $f(t)$ is a noise component which is commonly superimposed on the first Hall element and the second Hall element, the phase detection circuit detects a phase $\theta$ of the rotor by calculating:

$$\theta = \tan^{-1}(H1 \cdot \sin \alpha)/(H2/\beta - H1 \cdot \cos \alpha).$$

[Item 12] A sample analysis device capable of transferring and analyzing a liquid in a substrate for sample analysis loaded therein by rotating the substrate for sample analysis, the sample analysis device including:

a brushless motor to rotate the substrate for sample analysis, the brushless motor including a 2n-pole (n=1) rotor and a first Hall element and a second Hall element arranged at an angle $\alpha$ ($0° < \alpha < 180$) from each other with respect to a rotation axis of the rotor, the first Hall element and the second Hall element each outputting a voltage signal in accordance with a magnitude of a magnetic field of the rotor;

a driver circuit that drives the brushless motor; and the rotational angle detection circuit according to any one of items 1 to 11 that detects a rotational angle of the brushless motor.

[Item 13] A sample analysis device for transferring and analyzing a liquid in a substrate for sample analysis loaded therein by rotating the substrate for sample analysis, wherein:

a marker given a predetermined physical characteristic is provided at a predetermined position on the substrate for sample analysis, the sample analysis device including:

a brushless motor that rotates the substrate for sample analysis, the brushless motor including a 2n-pole (n: an integer of 1 or more) rotor and a first Hall element and a second Hall element arranged at an angle $\alpha$ ($0° < \alpha < 180°$) from each other with respect to a rotation axis of the rotor, the first Hall element and the second Hall element each outputting a voltage signal in accordance with a magnetic field of the rotor;

a driver circuit that controls how the brushless motor is driven;

an origin detection circuit that determines a position of the marker by detecting the predetermined physical characteristic so as to detect the position of the marker as an origin position; and the rotational angle detection circuit according to any one of items 1 to 8 to detect a rotational angle of the brushless motor, wherein:

a phase detection circuit of the rotational angle detection circuit detects a phase of the rotor at a point in time when the origin position is detected by the origin detection circuit; and an angle calculation circuit of the rotational angle detection circuit sets, as the predetermined reference angle, a phase of the rotor at the point in time so as to calculate a rotational angle of the rotor from the predetermined reference angle based on the phase detected by the phase detection circuit and the predetermined reference angle.

[Item 14] The sample analysis device according to item 13, wherein:

the marker is given a physical characteristic which enables optical identification thereof along a rotation direction of the substrate for sample analysis, the sample analysis device further including:

a light source; and a photodetector that detects light from the light source which has passed through the substrate for sample analysis when the light is radiated from the light source onto the substrate for sample analysis in rotation, wherein the origin detection circuit determines a position of the marker by detecting the physical characteristic based on a detection result of the photodetector.

[Item 15] The sample analysis device according to item 14, wherein:

the substrate for sample analysis includes, along the rotation direction, a portion having a first transmittance and another portion having a second transmittance different from the first transmittance; and the marker is the portion having the first transmittance.

[Item 16] The sample analysis device according to item 15, wherein the first transmittance is generally zero.

[Item 17] The sample analysis device according to item 14, wherein the photodetector is used as a photodetector to optically analyze the liquid in the substrate for sample analysis.

[Item 18] The sample analysis device according to any one of items 12 to 17, wherein the driver circuit stops rotation of the brushless motor based on the rotational angle of the brushless motor detected by the rotational angle detection circuit.

[Item 19] A rotational angle detection method for detecting a rotational angle of a brushless motor, wherein:

the brushless motor includes:

a 2n-pole (n: an integer of 1 or more) rotor; and a first Hall element and a second Hall element arranged in a positional relationship of an angle α (0°<α<180°) from each other with respect to a rotation axis of the rotor, the first Hall element and the second Hall element each outputting a voltage signal in accordance with a magnetic field of the rotor, the method including the steps of:

receiving the voltage signals output respectively from the first Hall element and the second Hall element;

detecting a phase of the rotor by using values of the voltage signals and information of the angle α; and calculating a rotational angle of the rotor calculated from an initial angle of the rotor based on the phase detected in the phase detecting step and a predetermined reference angle.

[Item 20] A computer program to detect a rotational angle of a brushless motor, wherein:

the brushless motor includes:

a 2n-pole (n: an integer of 1 or more) rotor; and a first Hall element and a second Hall element arranged in a positional relationship of an angle α (0°<α<180°) from each other with respect to a rotation axis of the rotor, the first Hall element and the second Hall element each outputting a voltage signal in accordance with a magnetic field of the rotor; and the computer program instructs a computer to execute the steps of:

receiving the voltage signals output respectively from the first Hall element and the second Hall element;

detecting a phase of the rotor by using values of the voltage signals and information of the angle α; and calculating a rotational angle of the rotor calculated from an initial angle of the rotor based on the phase detected in the phase detecting step and a predetermined reference angle.

A motor rotational angle detection circuit, a motor angle detection method, a sample analysis device and a computer program for a sample analysis device in one aspect of the embodiment of the present disclosure will now be described with reference to the accompanying drawings.

Embodiment 1

FIG. 1 shows a configuration of a sample analysis device 1 according to the present embodiment.

A substrate 10 for sample analysis, which has been loaded (set) in the sample analysis device 1, is rotated clockwise or counterclockwise, shaken and stopped at a predetermined position by the sample analysis device 1. Thus, the sample analysis device 1 can transfer, mix and analyze a liquid in a measurement chamber 12 in the substrate 10 for sample analysis. In order to rotate the substrate 10 for sample analysis at an intended rotation speed and stop the substrate 10 for sample analysis at an intended position, the sample analysis device 1 uses a marker 14 provided on the substrate 10 for sample analysis. The details of the detection process for detecting the rotational angle by using the marker 14 will be described below.

The sample analysis device 1 a brushless motor 20, a driver circuit 22, a rotational angle detection circuit 24, the control circuit 30, an origin detection circuit 32, an origin detection light source 34, a photoelectric conversion element 36, an optical measurement unit 38 and a display device 40. In the example configuration of the present disclosure, the substrate 10 for sample analysis will be described as not being a component of the sample analysis device 1 and as being able to be attached/detached to/from the sample analysis device 1. Components of the sample analysis device 1 will now be outlined below.

The brushless motor 20 is a motor including a permanent magnet rotor and a coil(s). It is assumed in the present embodiment, the rotor has two poles and the coils are three (3-phase). The brushless motor 20 is provided with a plurality of Hall elements to be described below.

The driver circuit 22 primarily includes an inverter circuit and a circuit for controlling the operation of the inverter circuit. The driver circuit 22 switches the current flow to the 3-phase coils of the brushless motor 20 in accordance with the rotation of the rotor of the brushless motor 20, thereby controlling the rotation of the brushless motor 20. A specific example configuration of the driver circuit 22 will be described below.

The rotational angle detection circuit 24 is an electronic circuit for detecting the rotational angle of the rotor by using the output voltage signals from a plurality of Hall elements and also by using the predefined arrangement of the Hall elements. The rotational angle detection circuit 24 can be implemented as an integrated circuit, for example.

The rotational angle detection circuit 24 includes a phase detection circuit 26 and an angle calculation circuit 28. The phase detection circuit 26 detects the current phase of the rotor by using the output voltage signals from a plurality of Hall elements, and information representing the predefined installment angle of the Hall elements. The angle calculation circuit 28 calculates the rotational angle of the rotor by using the rotational angle of the rotor, which has been calculated, and the current phase of the rotor.

Note that in the present specification, the phase of the rotor primarily means the absolute position (angle) of the rotor. The rotational angle of the rotor will be described as meaning the relative position (rotational angle) of the rotor with respect to the initial position (initial angle) of the rotor.

The control circuit 30 is a CPU provided in the sample analysis device 1, for example. The control circuit 30 executes a computer program loaded on the RAM (Random Access Memory; not shown), thereby sending instructions to other circuits in accordance with the procedure of the computer program. Circuits receiving instructions operate as will be described herein, thereby implementing the functions of the circuits. Instructions from the control circuit 30 are sent to the driver circuit 22, the rotational angle detection circuit 24, the optical measurement unit 38, the display device 40, etc., as shown in FIG. 1, for example. Procedures of the computer program are illustrated in the flow charts of the accompanying drawings.

Note that the RAM loaded with a computer program, in other words, the RAM storing a computer program, may be volatile or non-volatile. A volatile RAM is a RAM that cannot retain information stored thereon unless it is receiving power supply. For example, a dynamic random access memory (DRAM) is a typical volatile RAM. A non-volatile RAM is a RAM that can retain information without power supply thereto. For example, a magnetoresistance RAM (MRAM), a resistive RAM (ReRAM) and a ferroelectric memory (FeRAM) are example non-volatile RAMs. In the present embodiment, a non-volatile RAM is preferably employed. A volatile RAM and a non-volatile RAM are both examples of non-transitory computer-readable storage media. A magnetic storage medium such as a hard disk and an optical storage medium such as an optical disc are also examples of non-transitory computer-readable storage media. That is, the computer program of the present disclosure may be recorded on any of various non-transitory computer-readable media, other than media (transitory media) such as the air capable of propagating the computer program as a radio signal.

In the present specification, the control circuit 30 is described as being a separate component from the rotational angle detection circuit 24. However, they may be implemented by a piece of hardware. For example, a CPU (computer) provided in the sample analysis device 1 executes a computer program functioning as the control circuit 30 and a computer program functioning as the rotational angle detection circuit 24 in series or in parallel. Therefore, the CPU can be made to operate as an apparently different component.

The origin detection circuit 32 drives the origin detection light source 34 to radiate light and receive the output signal from the photoelectric conversion element 36. The origin detection circuit 32 determines whether or not a particular signal (origin signal) is included in the output signal, and detects the origin position of the sample analysis device 1, which has been set, by using the origin signal. The details of the origin position of the sample analysis device 1 will be described below with reference to FIG. 2.

The origin detection light source 34 is a light source, e.g., a light-emitting diode (LED), which radiates light of a predetermined wavelength. The photoelectric conversion element 36 is an element to detect light from the origin detection light source 34 by converting light into an electric signal, e.g., a photodiode. Note that this configuration is merely an example. As another example, a magnetic material may be provided instead of the marker 14 of the substrate 10 for sample analysis, and a magnetic detector may be provided instead of the photoelectric conversion element 36. Alternatively, the origin detection process itself is no longer needed if a structural restriction is provided such that the substrate 10 for sample analysis can be set in the sample analysis device 1 only in a particular position. This can also be applied to the 2n-pole (n is an integer of 2 or more) brushless motor 20 to be described in the embodiment below.

The optical measurement unit 38 is a device that allows the sample analysis device 1 to optically analyze and measure a sample having been injected into the measurement chamber 12 of the substrate 10 for sample analysis. The optical measurement unit 38 detects light emission (such as chemiluminescence, bioluminescence or electrochemiluminescence, for example) or fluorescent emission so as to quantitatively determine the concentration of the sample, etc. Note that the optical measurement unit 38 is merely an example configuration for detecting the light emission, and the present disclosure is not limited thereto. Various measurement methods may be used. One may use any configuration suitable for a measurement method such as fluorescent emission, optical absorbance, turbidity, light emission, etc.

The display device 40 is a liquid crystal display device, for example, for receiving and displaying a video signal output from the control circuit 30. Note that the display device 40 is described in the present specification as being provided in the sample analysis device 1. However, this configuration is merely an example. The display device 40 may be a device external to the sample analysis device 1.

Figure 2:
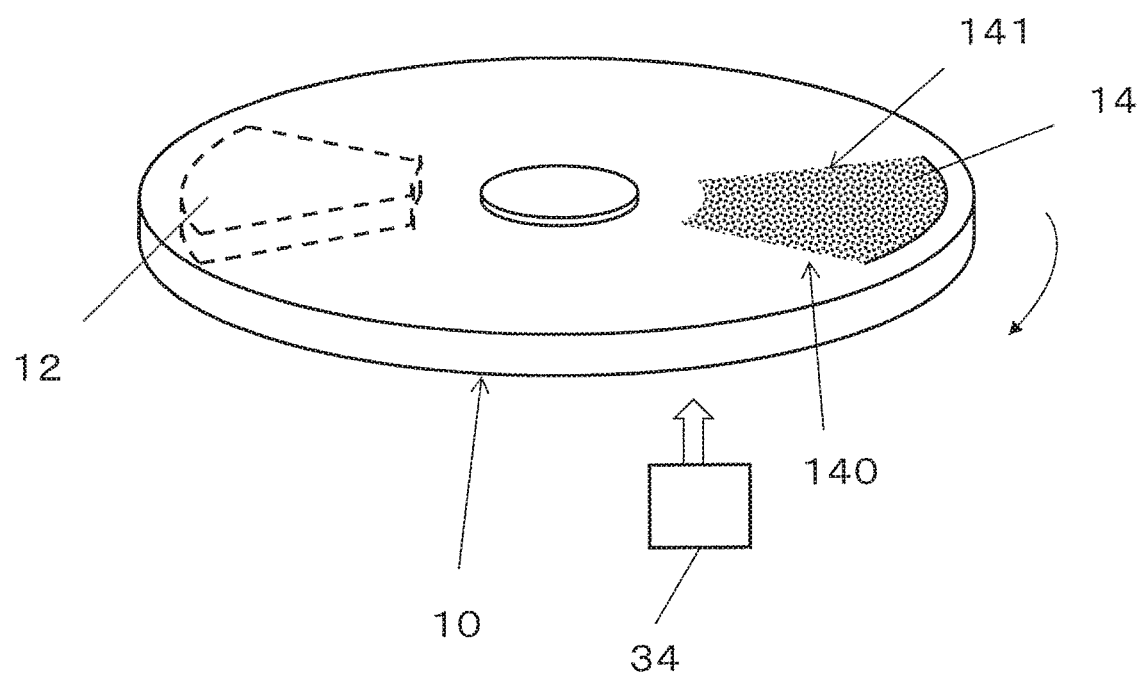
FIG. 2 A view showing an example configuration of a substrate 10 for sample analysis 10.

FIG. 2 shows an example configuration of the substrate 10 for sample analysis. In the present specification, the substrate 10 for sample analysis is a disc-shaped substrate having a predetermined thickness and having the measurement chamber 12 formed therein. Note that the substrate 10 for sample analysis does not need to be disc-shaped, but may be polygonal, e.g., rectangular, sector-shaped or hexagonal.

A sample is injected into the measurement chamber 12. The shape of the measurement chamber 12 illustrated is an example, and it may be any other shape. A plurality of measurement chambers 12 may be provided, and a channel connecting between measurement chambers may be provided.

The substrate 10 for sample analysis further includes the marker 14. The marker 14 does not allow light to pass therethrough, while other portions of the substrate 10 for sample analysis primarily allow light to pass therethrough. That is, the substrate 10 for sample analysis includes the marker 14 where the transmittance is generally zero, and other portions (other than the marker 14) where the transmittance is greater than zero (e.g., 60% or more).

In a situation where the origin detection light source 34 of the sample analysis device 1 is radiating light, the brushless motor 20 rotates the substrate 10 for sample analysis in the direction of an arrow in FIG. 2. The photoelectric conversion element 36 detects light up until an edge 140 of the marker 14, but does not detect light from the edge 140 to the other edge 141. The origin detection circuit 32 detects, as an origin signal, a decrease in the amount of light detected corresponding to the edge 140. Thus, the origin detection circuit 32 can determine the position of the marker 14. In the present specification, the position of the edge 140 of the marker 14 is treated as the origin position of the substrate 10 for sample analysis. Note that assuming that the marker 14 is sector-shaped, if the central angle thereof is smaller than the angular detection precision that is needed for analyzing the sample, the marker 14 itself may be defined as the origin position.

The origin position is used for the sample analysis device 1 to obtain information of the rotational angle of the substrate 10 for sample analysis. For example, assume that the sample analysis device 1 pre-stores information of the substrate 10 for sample analysis to be set. By continuously detecting information of the rotational angle of the substrate 10 for sample analysis, the sample analysis device 1 can control the rotation, shaking, and the position to stop the rotation of the substrate 10 for sample analysis. Thus, it is possible to appropriately mix a plurality of samples having been injected into the measurement chamber 12, and to stop the rotation of the substrate 10 for sample analysis at a rotational position that is suitable for the measurement by the optical measurement unit 38.

Figure 3:
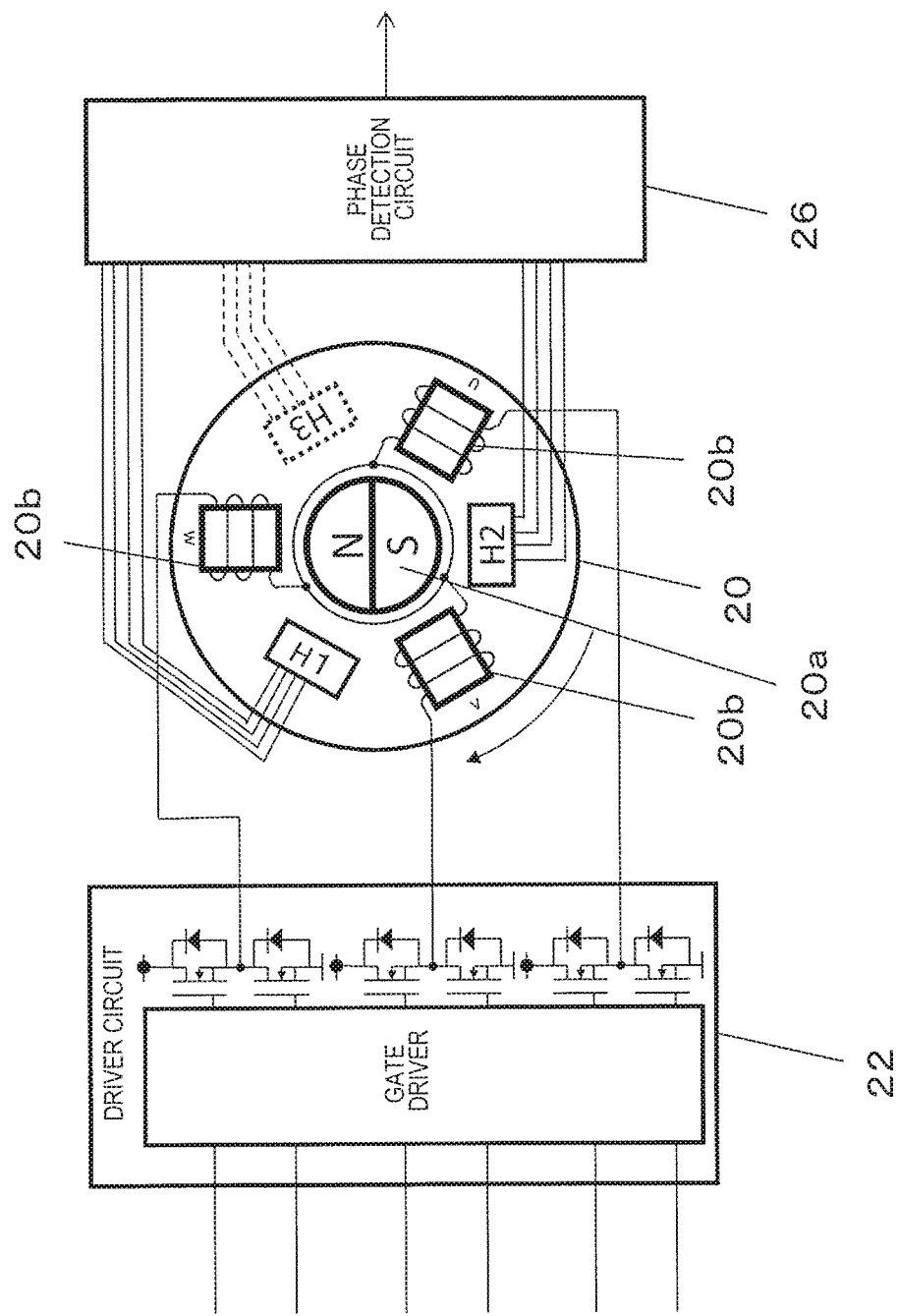
FIG. 3 An example diagram showing an example configuration of a brushless motor 20 and a driver circuit 22, and a connection relationship between the brushless motor 20, the driver circuit 22 and a phase detection circuit 26.
Figure 4:
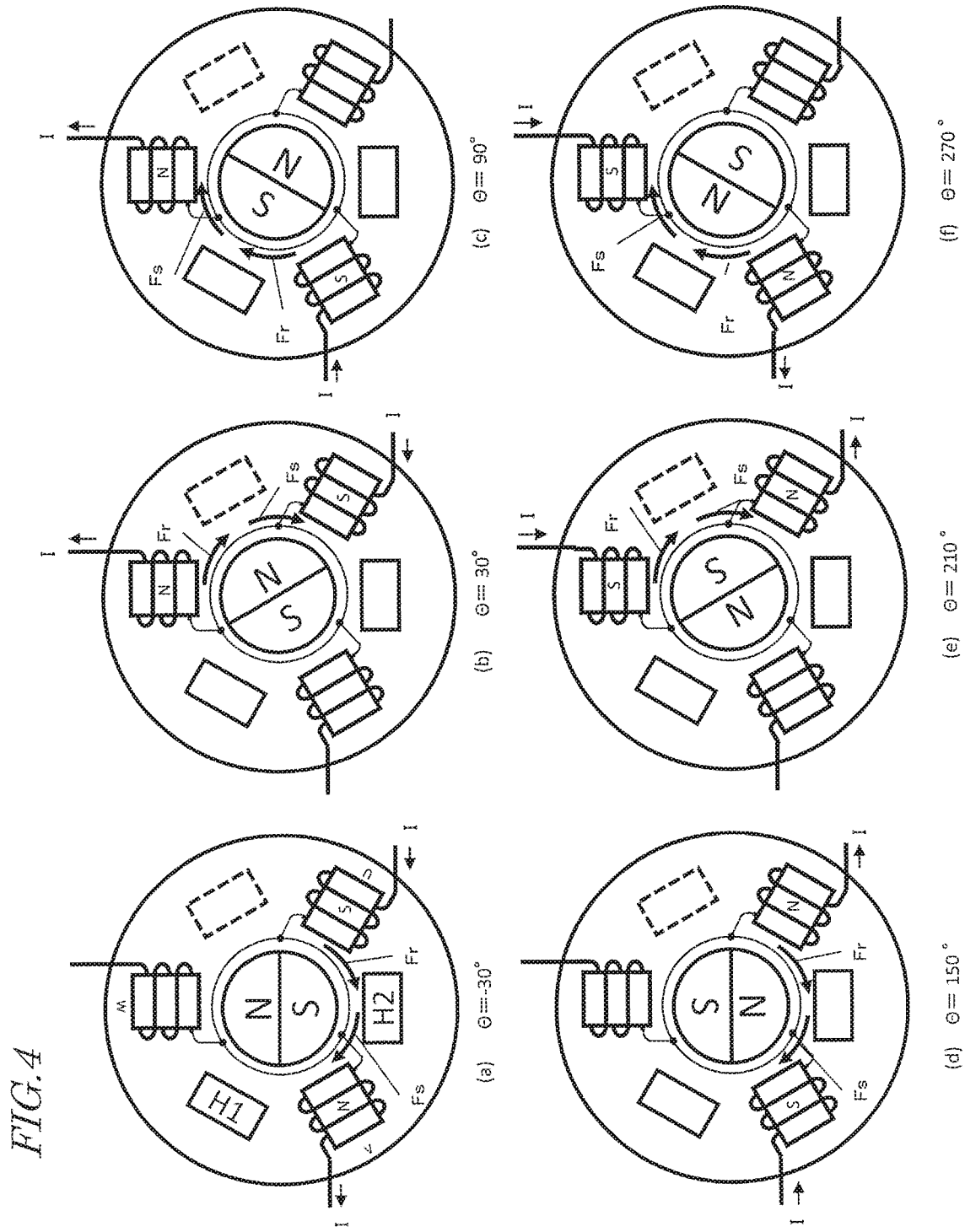
FIG. 4 (a) to (f) are diagrams showing an example operation during forward rotation of the brushless motor 20.

FIG. 3 shows an example configuration of the brushless motor 20 and the driver circuit 22, and a connection relationship between the brushless motor 20, the driver circuit 22 and the phase detection circuit 26.

As described above, in the present embodiment, the brushless motor 20 is of 2-pole, 3-phase type. The brushless motor 20 includes a rotor 20a having two poles (the north pole and the south pole) provided at the center thereof. Three coils 20b for the U, V and W phase are provided at an interval of 120° while being centered about the rotor 20a. It is assumed in the present embodiment that the clockwise rotation indicated by an arrow is the forward rotation, and the counterclockwise rotation is the reverse rotation. This similarly applies to the rotation direction of the substrate 10 for sample analysis.

Moreover, the brushless motor 20 includes Hall elements H1 to H3. In the present embodiment, an example where two Hall elements H1 and H2 are used will be described. Note however that three Hall elements may be used as shown in the figure. The Hall elements H1 and H2 are also arranged at an interval of 120° while being centered about the rotor 20a.

The driver circuit 22 includes an inverter circuit formed by transistors, and a gate driver thereof. Based on instructions from the control circuit 30 to be received from the left side of the figure, to be input from the left side of the figure, the driver circuit 22 controls the rotation direction, the rotation speed, etc., of the brushless motor 20 by adjusting the direction and the level of the current flow through each of the three coils 20b of the U, V and W phase.

The phase detection circuit 26 receives the output voltage signals of the Hall elements H1 to H3 and detects the phase of the rotor 20a. A specific operation of the phase detection circuit 26 will be described below.

FIG. 4(a) to FIG. 4(f) show an example operation during forward rotation of the brushless motor 20. FIG. 4(a) to FIG. 4(f) show the direction of the current I flowing through the coils 20b, and the direction of the repulsive force Fr and the attractive force Fs given by the coils 20b to the rotor 20a at different positions reached by varying the phase of the rotor 20a clockwise by 60° starting from −30°.

Figure 5:
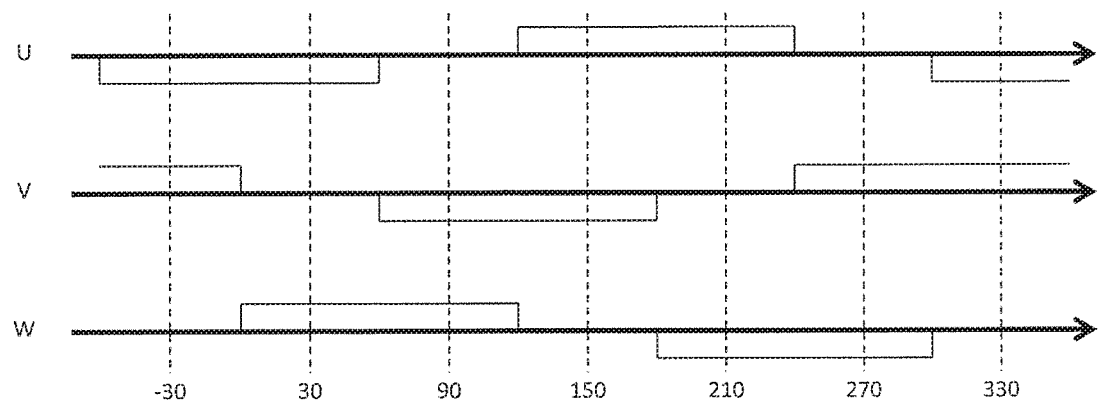
FIG. 5 A diagram schematically showing an example waveform pattern of a drive current when the brushless motor 20 is rotated in forward rotation.
Figure 6:
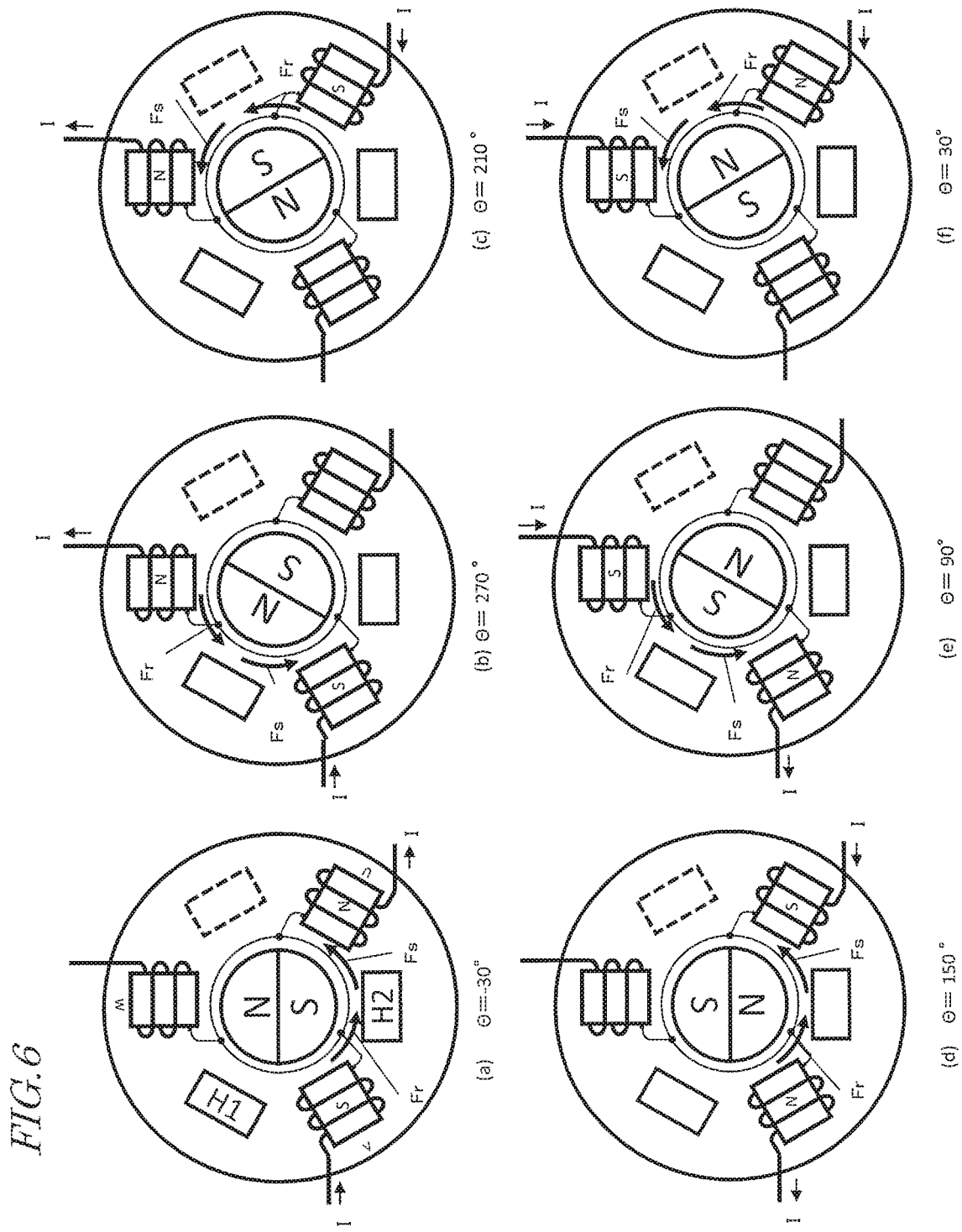
FIG. 6 (a) to (f) are diagrams showing an example operation during reverse rotation of the brushless motor 20.

FIG. 5 schematically shows the waveform pattern of the drive current at different phase angles of different coil phases (U, V and W) while the brushless motor 20 is in forward rotation. The time axis is drawn from left to right. The driver circuit 22 controls the direction and the polarity of the drive current depending on the phase. Forward rotation of the rotor 20a is realized by providing drive currents to the coils 20b in the waveform patterns shown in FIG. 5.

FIG. 6(a) to FIG. 6(f) show an example operation during reverse rotation of the brushless motor 20. FIG. 6(a) to FIG. 6(f) show the direction of the current flowing through the coils 20b, and the direction of the repulsive force and the attractive force given by the coils 20b to the rotor 20a at different positions reached by varying the phase of the rotor 20a counterclockwise by 60° starting from −30°.

Figure 7:
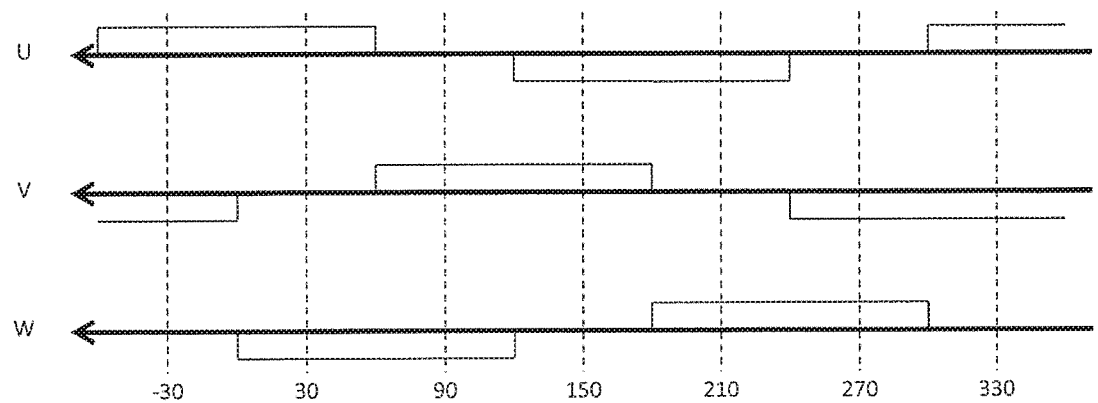
FIG. 7 A diagram schematically showing an example waveform pattern of a drive current when the brushless motor 20 is rotated in reverse rotation.

FIG. 7 schematically shows the waveform pattern of the drive current at different phase angles of different coil phases (U, V and W) while the brushless motor 20 is in reverse rotation. The time axis is drawn from left to right. The driver circuit 22 controls the direction and the polarity of the drive current depending on the phase. Forward rotation of the rotor 20a is realized by providing drive currents to the coils 20b in the waveform patterns shown in FIG. 5.

Figure 8:
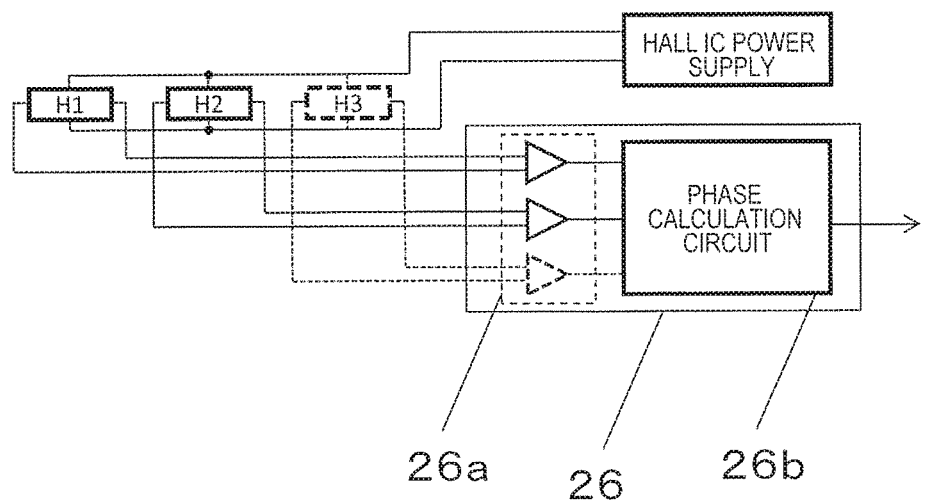
FIG. 8 A diagram showing an example configuration of the phase detection circuit 26 connected to Hall elements H1 to H3.

FIG. 8 shows an example configuration of the phase detection circuit 26 connected to the Hall elements H1 to H3. FIG. 8 also shows the Hall IC power supply to provide current flows through the Hall elements.

The phase detection circuit 26 includes an AD converter 26a which converts analog voltage signals output from the Hall elements H1 to H3 into digital signals, and a phase calculation circuit 6b which calculates the phase of the rotor 20a by using the voltage signals, which have been converted by the AD converter 26a into digital signals. The details of the phase calculation will be described below.

Figure 9:
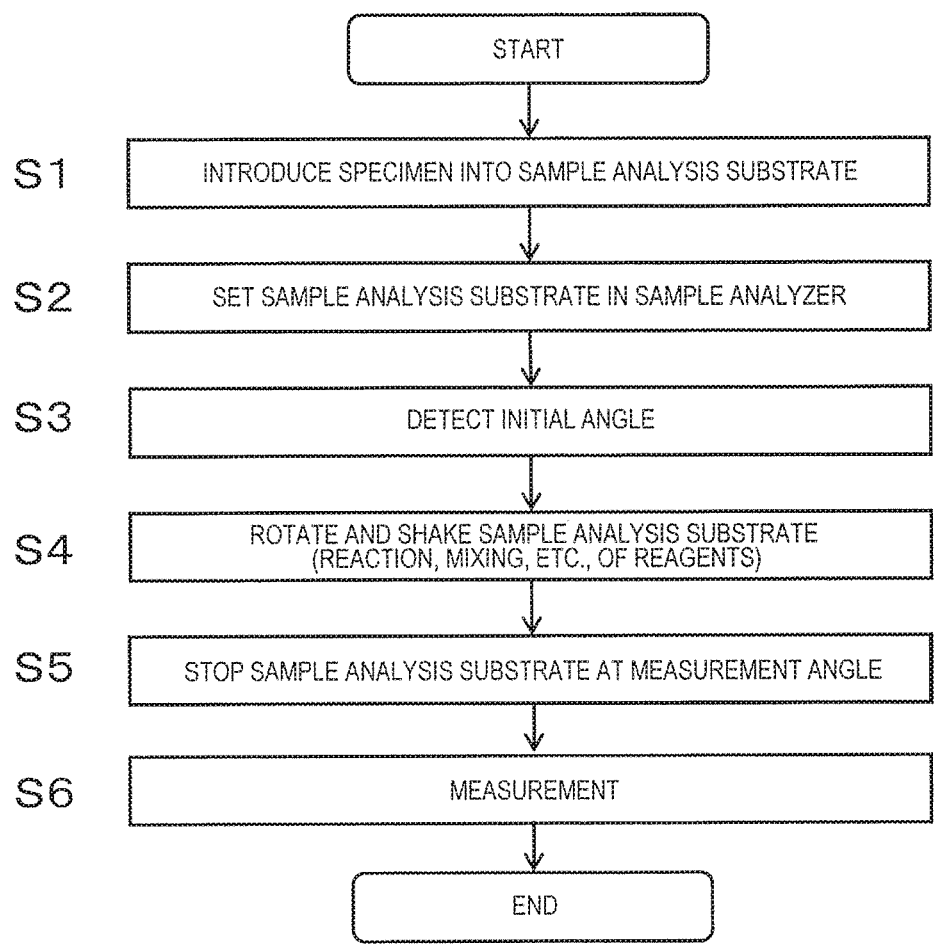
FIG. 9 A flow chart showing an example procedure for measuring a sample using the sample analysis device 1.

FIG. 9 shows a procedure for measuring a sample using the sample analysis device 1. Steps S1 and S2 are operations performed by the user of the sample analysis device 1, and step S3 and the subsequent steps are operations performed by the sample analysis device 1.

In step S1, the user introduces a sample, to be the analyte, into the substrate 10 for sample analysis. In step S2, the user sets the substrate 10 for sample analysis in the sample analysis device 1. Through this operation, the phase relationship between the substrate 10 for sample analysis and the rotor 20a is fixed.

In step S3, the phase detection circuit 26 of the sample analysis device 1 detects the initial angle of the rotor 20a. The details of this process will be described below with reference to FIG. 10.

In step S4, the control circuit 30 of the sample analysis device 1 rotates and shakes the substrate 10 for sample analysis for reaction, mixing, etc., of the reagents in the sample. Note that rotation includes forward rotation and reverse rotation. Shaking is an operation of stopping the substrate 10 for sample analysis, and then periodically switching the rotation direction of the substrate 10 for sample analysis back and forth within a predetermined angular range.

In step S5, the control circuit 30 of the sample analysis device 1 stops the rotation of the substrate 10 for sample analysis at an angle suitable for measurement. The angle suitable for measurement is preset in the sample analysis device 1 based on, for example, the position of the measurement chamber 12 of the substrate 10 for sample analysis. Note that the type of the substrate 10 for sample analysis may be identified so that the control circuit 30 sets the angle, etc., depending on the substrate for sample analysis which has been set. The process of identifying the type of the substrate 10 for sample analysis may be performed automatically by reading a barcode on the upper surface, the lower surface or the side surface of the substrate 10 for sample analysis, for example, or the user may input the type of the substrate 10 for sample analysis to be set by using an input device (not shown) such as a touch panel or a keyboard.

In step S6, the optical measurement unit 38 of the sample analysis device 1 performs an optical measurement. In the present disclosure, there is no particular limitation on the process regarding the measurement of the sample, and the detailed description thereof is omitted.

Figure 10:
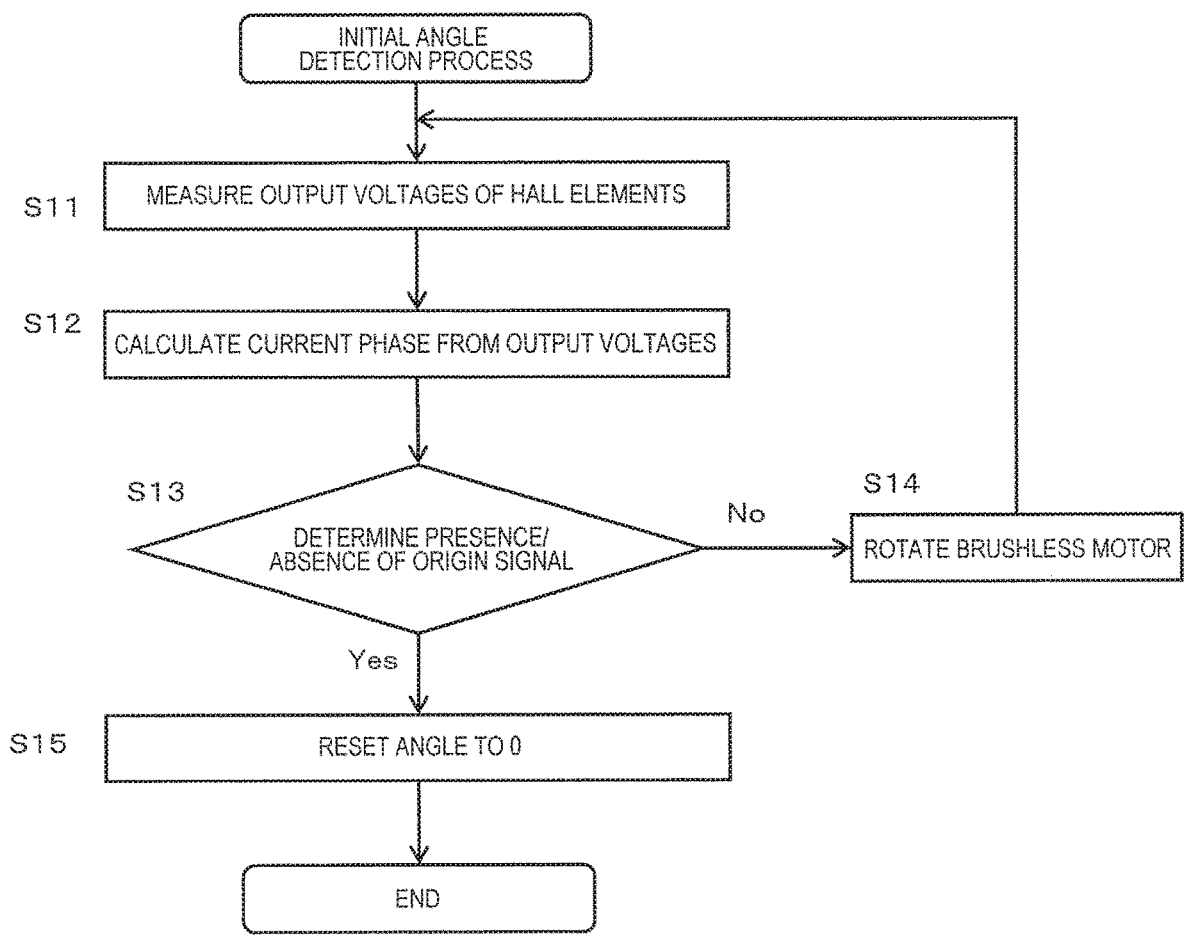
FIG. 10 A flow chart showing an example procedure for the process in which an initial angle of the substrate 10 for sample analysis is detected by the sample analysis device 1.

FIG. 10 shows the procedure for the process of detecting the initial angle of the substrate 10 for sample analysis performed by the sample analysis device 1.

In step S11, the phase detection circuit 26 measures the output voltages of the Hall elements H1 and H2. Note that although this process is performed by a phase calculation circuit 26b (FIG. 8), it is discussed in the following description that the phase detection circuit 26 performs this process.

Figure 11:
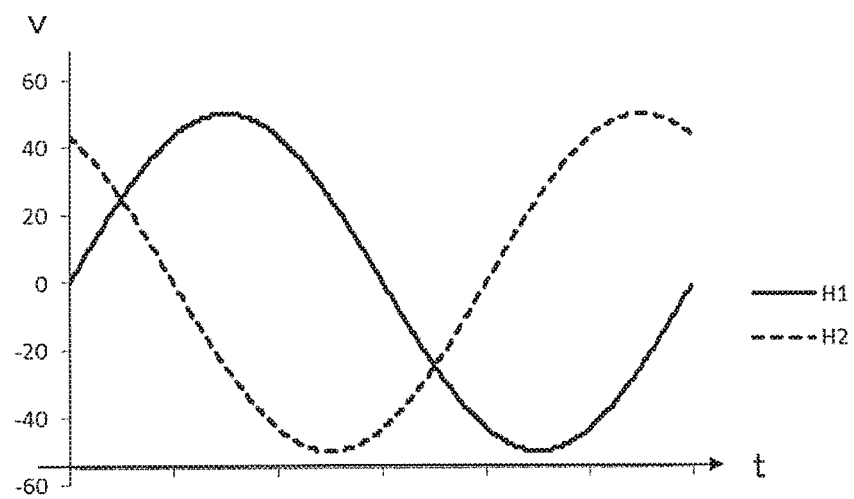
FIG. 11 A graph showing example voltage signal waveforms of the Hall elements H1 and H2.

FIG. 11 shows example voltage signal waveforms of the Hall elements H1 and H2. The horizontal axis represents time (t), and the vertical axis represents the voltage of the Hall elements. Although the phase detection circuit 26 obtains and processes the output voltage waveforms as digital signals as described above, analog signal waveforms are used in the example to be described in the present specification. In practice, analog signal waveforms as shown in the figure are sampled at a predetermined sampling rate and the sampled values are quantized to obtain voltage values.

The Hall elements are also influenced by the magnetic field, which is produced as the coils of the U, V and W phase of the brushless motor 20 are energized. Therefore, the voltage values detected by the Hall elements include offset values superimposed thereon. The amount of energization of the coils varies depending on the phase, the rotation direction, or the like. If the sampling is done while the coils are energized, the offset value varies, which will increase the error in the phase calculation. Therefore, the driver circuit 22 performs a control such that the energization is stopped for all the coils while the sampling is done (at the time of sampling). Then, it is possible to improve the precision of phase calculation.

Note that the driver circuit 22 drives the brushless motor by energizing the coils with the same energization pattern while the sampling is done (at the time of sampling). Then, the offset value is stabilized, thereby improving the precision of phase calculation. That is, the driver circuit 22 drives in such a manner that the potentials at the terminals corresponding to the U, V and W phase of the brushless motor 20 (the U terminal, the V terminal and the W terminal) are all zero so that the amount of energization of the coils does not vary while the sampling is done (at the time of sampling). Or, the driver circuit 22 may make the potentials at the U terminal, the V terminal and the W terminal all coincide with the power supply voltage. Alternatively, the driver circuit 22 may make only the potential at the U terminal, for example, coincide with the power supply voltage, while making the potentials at the V terminal and the W terminal zero. The offset value can be stabilized by applying a voltage to the coils in such a manner that the pattern of voltage application is always constant while the sampling is done (at the time of sampling).

In step S12 of FIG. 10, the phase detection circuit 26 calculates the current phase from the output voltages. Now, the details of the phase calculation according to the present embodiment will be described. First, the principle of phase calculation will be described, and then a specific process will be described with reference to FIG. 13.

Now, assume that the output of the Hall element H1 is denoted as H1=A sin ωt, and the output of the Hall element H2 as H2=A sin(ωt+α). As described above, the Hall elements H1 and H2 are arranged in a positional relationship of 120° with respect to each other while being centered about the rotor 20a. Thus, α=120°.

The phase detection circuit 26 calculates the phase ωt of the rotor 20a by Equation 1 below. Note that w is the angular velocity of the rotor 20a, and $t$ is time.

$$H_1 = A\sin\omega t$$ [Equation 1]

$$H_2 = A\sin(\omega t + \alpha)$$
$$= A(\sin\omega t\cos\alpha + \cos\omega t\sin\alpha)$$

$$A\cos\omega t = \frac{H_2 - H_1\cos\alpha}{\sin\alpha}$$

$$\tan^{-1}\frac{\sin\omega t}{\cos\omega t} = \tan^{-1}\frac{A\sin\omega t}{A\cos\omega t}$$
$$= \tan^{-1}\frac{H_1 \times \sin\alpha}{H_2 - H_1\cos\alpha}$$

Equation 1 will be explained. First, the equation of the Hall element H2 is deformed. Resultant A cos ωt is expressed by the equation on the fourth line including H1 and H2.

Figure 12:
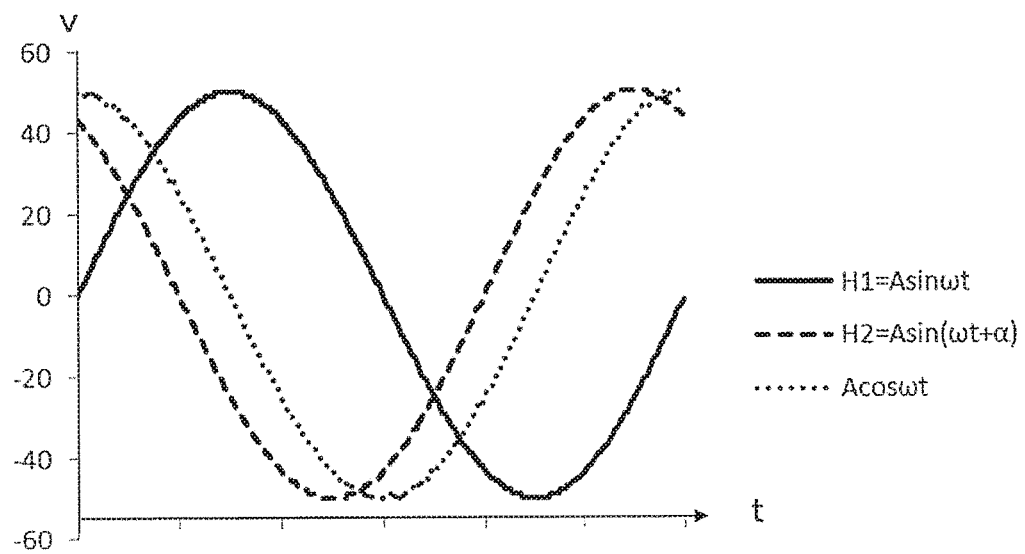
FIG. 12 A graph showing an example relationship between the voltage signal waveforms of the Hall elements H1 and H2 and the waveform of $\cos \omega t$.

FIG. 12 shows the relationship between the voltage signal waveforms of the Hall elements H1 and H2 and the waveform of cos ωt. The horizontal axis represents time (t), and the vertical axis represents the voltage (v) of the Hall elements. The phase detection circuit 26 calculates A cos ωt by the equation on the fourth line above.

The phase ωt to be determined can be obtained as the inverse tangent (arc tangent) of (sin ωt/cos ωt). By Equation 1, it is represented as an equation using the outputs H1 and H2 of the Hall elements and the positional relationship (α) between the outputs H1 and H2 of the Hall elements. The phase detection circuit 26 obtains the phase of the rotor 20a by using the outputs H1 and H2 of the Hall elements and information of the angle α known in advance.

Figure 13:
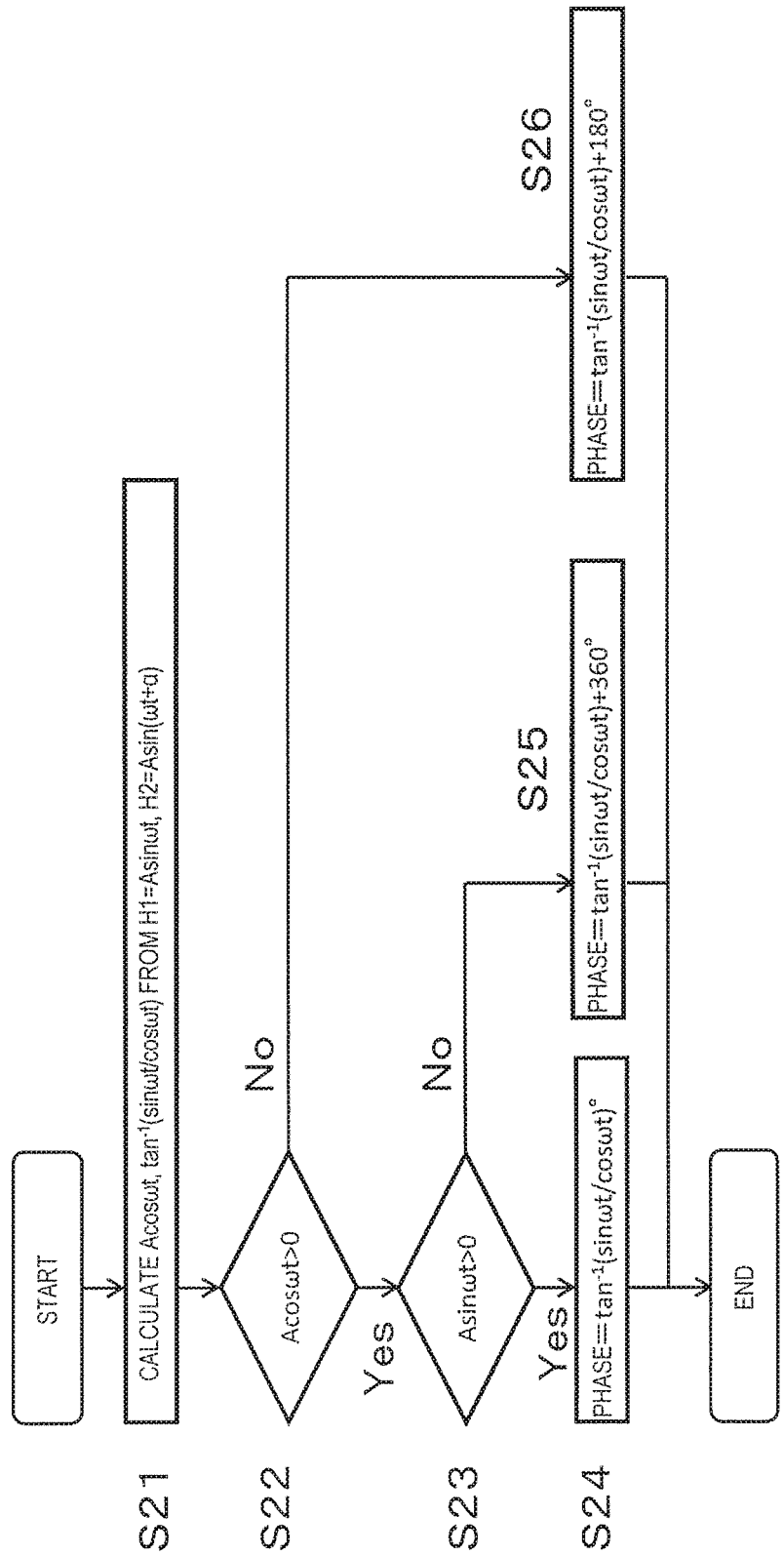
FIG. 13) A flow chart showing an example procedure for a phase calculation process of the phase detection circuit 26.

FIG. 13 shows the details of step S12 of FIG. 10. FIG. 13 shows the procedure for the phase calculation process of the phase detection circuit 26.

In step S21, the phase detection circuit 26 calculates A cos ωt, tan$^{-1}$(sin ωt/cos ωt) from H1=A sin ωt, H2=A sin(ωt+α). The angle α is a given value obtained from the arrangement of the Hall elements H1 and H2.

In step S22 and step S23, the signs of A cos ωt and A sin ωt are determined. These processes are provided based on the fact that the phase is calculated using the arc tangent, and the process is varied depending on the quadrant of the phase ωt.

Specifically, if A cos ωt>0 and A sin ωt>0, the phase detection circuit 26 obtains, as the phase, the calculated value of tan$^{-1}$(sin ωt/cos ωt) (step S24).

If A cos ωt>0 and A sin ωt≤0, the phase detection circuit 26 obtains, as the phase, a value obtained by adding 360° to the calculated value of tan$^{-1}$(sin ωt/cos ωt) (step S25).

If A cos ωt<0, the phase detection circuit 26 obtains, as the phase, a value obtained by adding 180° to the calculated value of tan$^{-1}$(sin ωt/cos ωt) (step S26).

Figure 14:
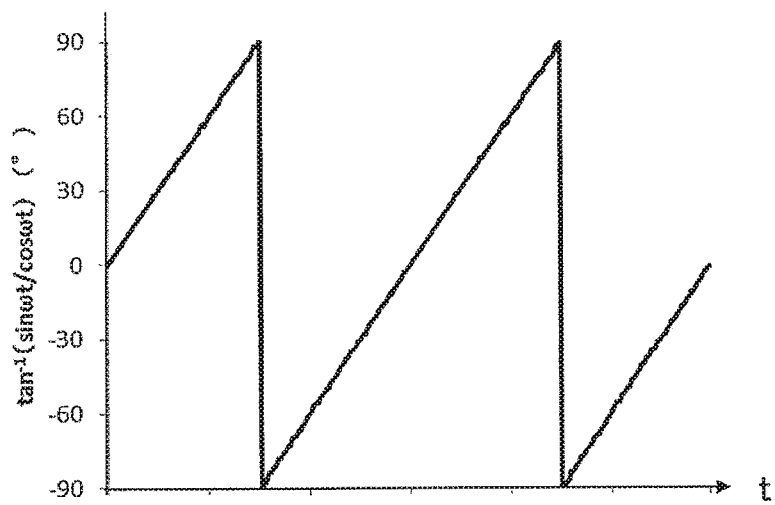
FIG. 14 A graph showing an example waveform of $\tan^{-1}(\sin \omega t/\cos \omega t)$ calculated by the phase detection circuit 26.

FIG. 14 shows the waveform of tan$^{-1}$(sin ωt/cos ωt) calculated by the phase detection circuit 26. Note that since the arc tangent does not have a value at ±90°, it is a discrete function. Note that the waveform of FIG. 14 is schematically shown for the purpose of illustration.

The sign of the arc tangent is reversed at phases of 90° and −90°. The range from 0° to 90° corresponds to A cos ωt>0 and A sin ωt>0 in steps S22 and S23 of FIG. 13, and the process of step S24 is performed. The following range from −90° to 0° in practice corresponds to 90° to 180°. That is, this corresponds to A cos ωt<0 in step S22 of FIG. 13, and the process of step S26 is performed. The range from −90° to 0° for the second iteration corresponds to the range from 270° to 360°. That is, this corresponds to A cos ωt>0 and A sin ωt≤0 in steps S22 and S23 of FIG. 13, and the process of step S25 is performed.

Figure 15:
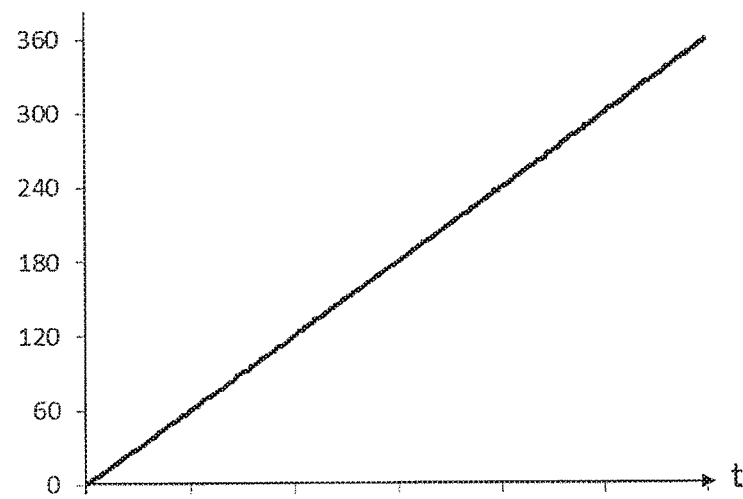
FIG. 15 A graph showing an example phase of a rotor 20a obtained by the process of FIG. 13.

FIG. 15 shows the phase of the rotor 20a obtained by the process of FIG. 13. As a result, it is understood that the phase changes continuously from 0° to 360° in proportion to time.

Through the process described above, the process of step S12 in FIG. 10 is realized, and the phase detection circuit 26 detects the current phase of the rotor 20a.

Reference is again made to FIG. 10.

Figure 16:
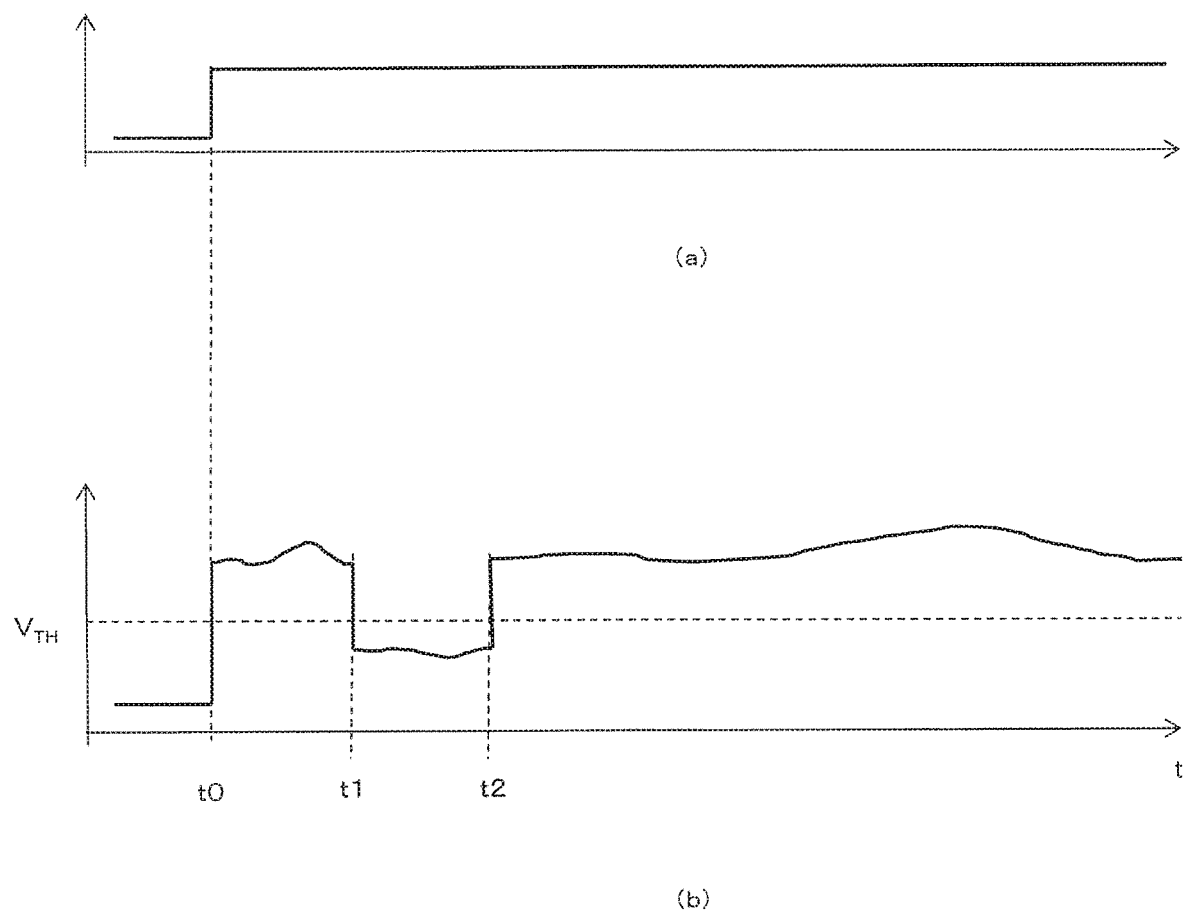
FIGS. 16 (a) and (b) are timing charts illustrating an example operation of an origin detection circuit 32.

In step S13, the origin detection circuit 32 determines the presence/absence of the origin signal. Referring to FIG. 16, the determination process will be described in detail.

FIG. 16(a) and FIG. 16(b) are timing charts illustrating the operation of the origin detection circuit 32. FIG. 16(a) shows the output of the origin detection light source 34, and FIG. 16(b) shows the light detection waveform obtained by the photoelectric conversion element 36. The origin detection is performed by detecting the marker 14 while rotating the substrate 10 for sample analysis.

First, at time t=t0, light is radiated from the origin detection light source 34. It is assumed that the substrate 10 for sample analysis is already rotating at time t=t0. In the beginning, light passes through a portion of the substrate 10 for sample analysis other than the marker 14 to be detected by the photoelectric conversion element 36. Then, the detected value exceeds a predetermined threshold value Vth.

Then, at time t=t1, light is blocked by the edge 140 of the marker 14 of the substrate 10 for sample analysis. Therefore, the detected value of the photoelectric conversion element 36 falls below the threshold value Vth. The decrease in the detected value continues until the other edge 141 is reached at time t=t2.

Past the other edge 141 at time t=t2, light again passes through the substrate 10 for sample analysis to be detected by the photoelectric conversion element 36. Then, the detected value exceeds a predetermined threshold value Vth. The period in which the detected value exceeds the threshold value Vth continues until the substrate 10 for sample analysis makes one rotation so that light is again blocked by the marker 14.

When light is radiated from the origin detection light source 34 but the detected value of the photoelectric conversion element 36 exceeds the threshold value Vth, the origin detection circuit 32 determines that the origin signal is absent, and the process of step S14 is performed following step S13. In step S14, the control circuit 30 instructs the driver circuit 22 to further rotate the brushless motor 20.

When light is radiated from the origin detection light source 34 and the detected value of the photoelectric conversion element 36 falls below the threshold value Vth, the origin detection circuit 32 determines that the origin signal is present, and the process of step S15 is performed following step S13.

In step S15, the origin detection circuit 32 resets the angle to zero in response to the detection of the origin signal. This process means that the origin position is set as the initial angle. Note that the process of resetting the angle to zero may be performed by the angle calculation circuit 28 to be described below. Note that although the initial angle is set to zero, the phase of the rotor 20a when the origin position is detected may be stored and used as the phase $\theta0$. The present embodiment will be described by using the phase $\theta0$ for the purpose of generalization.

By the process described above, the initial angle is detected (step S3 of FIG. 9), and the angle of the substrate 10 for sample analysis with respect to the origin position is set as the initial angle.

Figure 17:
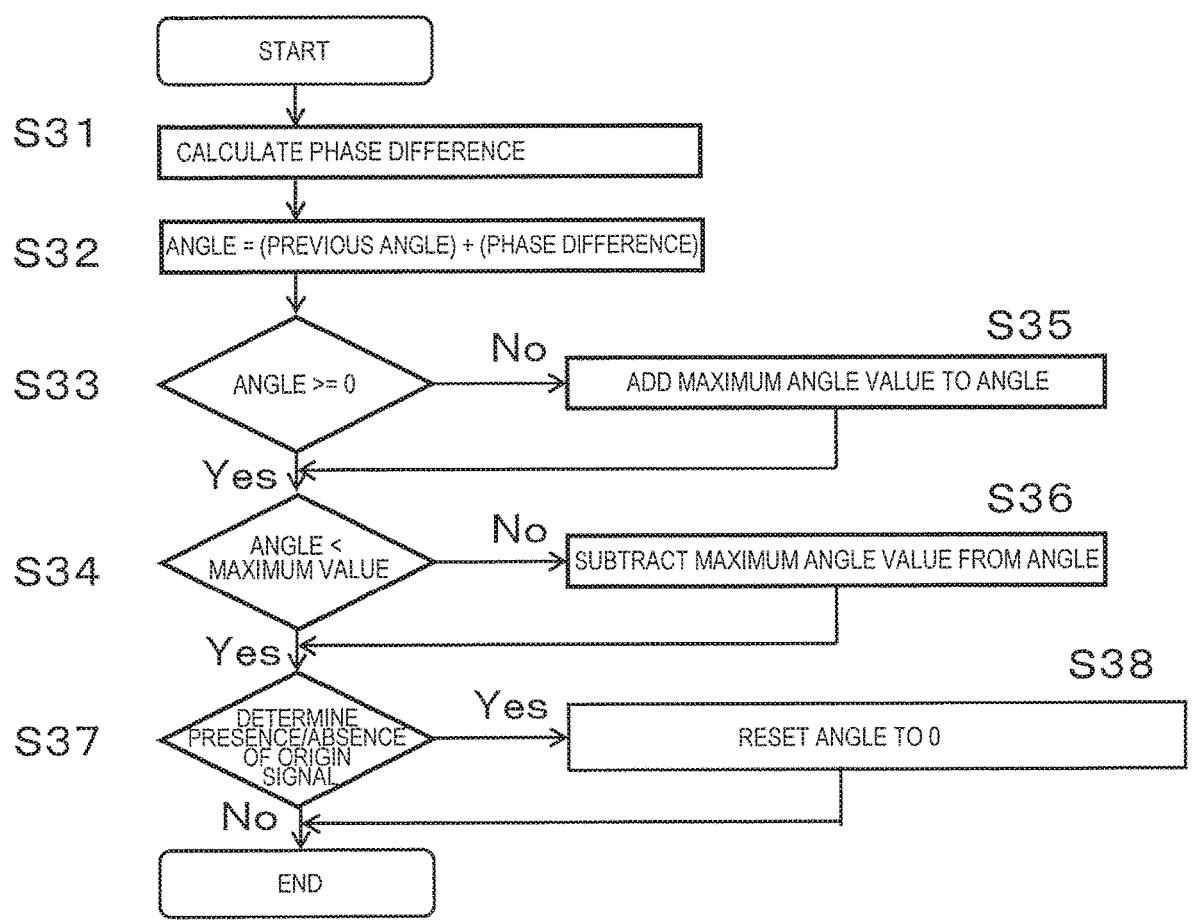
FIG. 17 A flow chart showing an example procedure for the process of an angle calculation circuit 28.

FIG. 17 shows the procedure for the process of the angle calculation circuit 28. The angle calculation circuit 28 can detect the rotational angle of the rotor 20a, by the procedure shown in the figure, by using the phase of the rotor 20a.

The angle calculation circuit 28 calculates the phase difference in step S31, and calculates the rotational angle of the rotor 20a in step S32. The rotational angle is the sum between the angle of the rotor 20a calculated in the previous iteration and the phase difference calculated in step S31.

Figure 18:
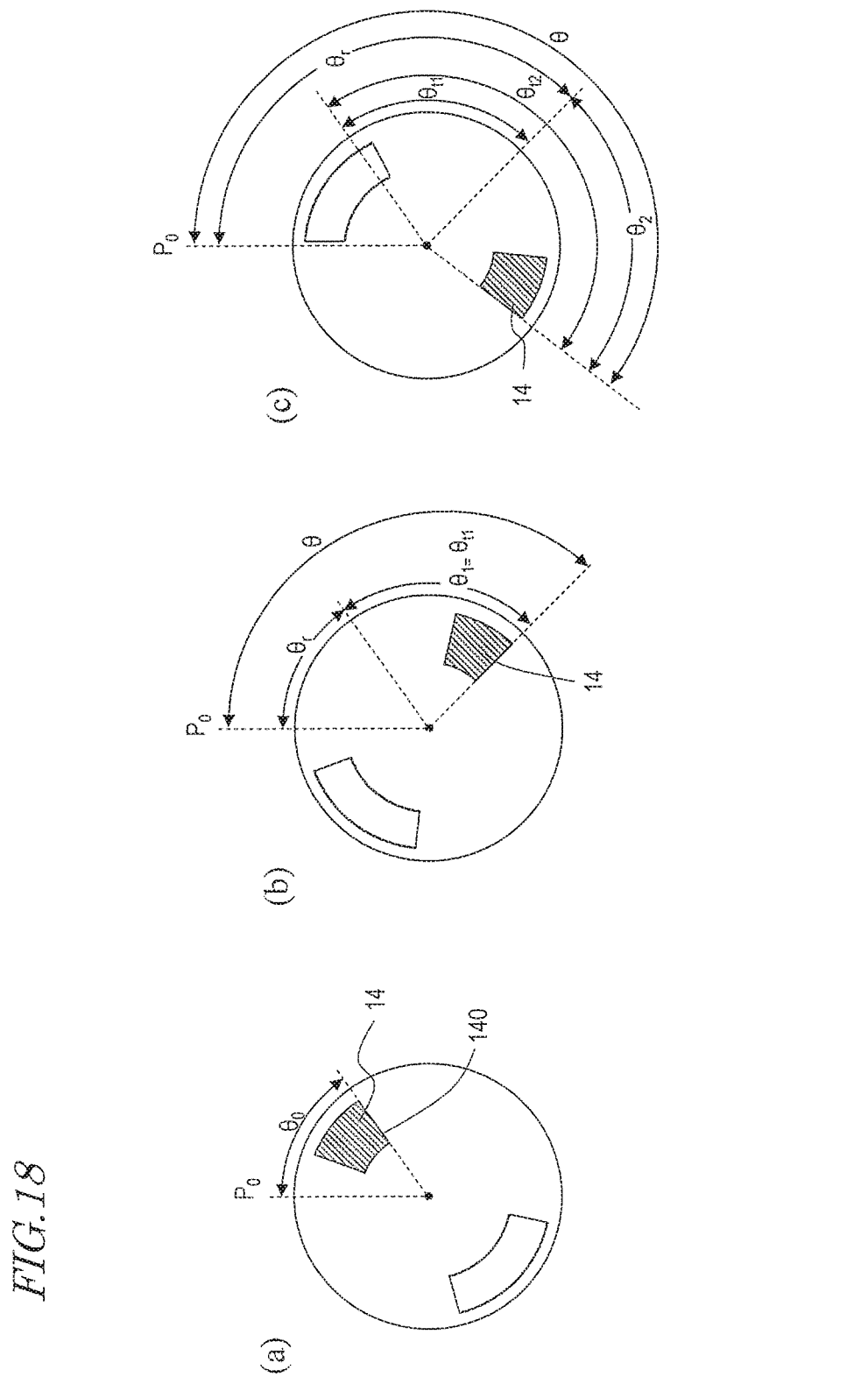
FIG. 18 (*a*) to (*c*) are diagrams showing an example rotation of the substrate 10 for sample analysis for illustrating the calculation process of the angle calculation circuit 28.

Referring now to FIG. 18, the process of steps S31 and S32 will be described in detail.

FIG. 18(a) to FIG. 18(c) show an example rotation of the substrate 10 for sample analysis for illustrating the calculation process of the angle calculation circuit 28.

For the calculation, the angle calculation circuit 28 uses variables $\theta$, $\theta n$, $\theta tn$ (integers of n=0 or more), and $\theta r$. First, reference is made to FIG. 18(a) to FIG. 18(c). FIG. 18(a) to FIG. 18(c) show rotational positions of the substrate 10 for sample analysis at time t=0, 1 and 2, for example. The position P0 is defined on the sample analysis device 1 for the purpose of discussion, and the initial phase is measured from the position P0.

The variable $\theta$ represents the phase of the rotor 20a at measurement time t. FIG. 18(b) and FIG. 18(c) show the angle $\theta$ at time t=1 and 2.

The variable $\theta n$ represents the angle by which the rotor 20a has rotated since the time of the $(n-1)^{th}$ measurement until the time of the $n^{th}$ measurement. $\theta 0$ is the initial phase of the rotor 20a. Although it is typically zero as a result of resetting in step S15 of FIG. 10, the generalized denotation $\theta 0$ is used in the following description. The initial phase $\theta 0$ is represented by the initial angle about the rotation axis from the position P0 to the edge 140 of the marker 14 when the substrate 10 for sample analysis is set in the sample analysis device 1. FIG. 18(b) and FIG. 18(c) show $\theta 1$ and $\theta 2$.

The variable $\theta tn$ represents the total sum angle over which the rotor 20a has rotated by time tn. Using the initial phase of the rotor 20a as a reference, the rotational angle is represented as the amount of displacement from the initial phase. The variable $\theta tn$ is the rotational angle of the substrate 10 for sample analysis to be obtained.

The variable $\theta r$ represents the phase of the rotor 20a obtained in the measurement in the previous iteration. In other words, when measuring the rotational angle at time t, the variable $\theta r$ represents the phase of the rotor 20a at immediately-preceding time (t−1).

FIG. 18(a) shows the relationship between the phase (initial phase) $\theta 0$ and the position of the marker 14 at t=0. Substitute 0 into $\theta tn$ and substitute $\theta 0$ into $\theta r$. They are expressed as $\theta t0 \rightarrow 0$ and $\theta r \leftarrow \theta 0$, respectively.

FIG. 18(b) shows the substrate 10 for sample analysis, which has been rotated by the angle $\theta 1$. At this point, $\theta 1 = \theta - \theta r$ and $\theta t1 = \theta t0 + \theta 1 = \theta 1 = \theta - \theta r$ hold true. Then, $\theta r \leftarrow e$. Thus, $\theta r$, which is the value of $\theta 0$, is updated to $\theta$.

FIG. 18(c) shows the substrate 10 for sample analysis, which has been further rotated by the angle $\theta 2$. At this point, $\theta 2 = \theta - \theta r$ and $\theta t2 = \theta t1 + \theta 2$ hold true. Then, $\delta \theta r \leftarrow \theta$.

With variables and calculations described above, the angle $\theta tn$ to be obtained can be expressed by the following equation.

$$\theta tn = \theta t(n-1) + \theta n$$

This equation corresponds to the formula of step S32 of FIG. 17. The rotational angle $\theta tn$ of the substrate 10 for sample analysis to be obtained is represented by the previous rotational angle $\theta t(n-1)$ and the amount of change in phase (the difference between the current phase and the previous phase). Note that the value of the variable $\theta n$ of this equation can be either positive or negative. This is because the brushless motor 20 is capable of both forward rotation and reverse rotation.

In step S33 of FIG. 17, the angle calculation circuit 28 determines whether or not the rotational angle obtained in step S32 is 0° or more. If the rotational angle is 0° or more, the process proceeds to step S34, and if it is less than 0°, the process proceeds to step S35.

In step S34, the angle calculation circuit 28 determines whether or not the rotational angle is less than a predetermined maximum value (e.g., 360°). If it is greater than or equal to the maximum value, the process proceeds to step S36, and if it is less than the maximum value, the process proceeds to step S37.

In step S36, the angle calculation circuit 28 adds the maximum value (e.g., 360°) to the rotational angle, and adjusts the value of the rotational angle so that it is within the range from 0° to 360°.

In step S37, the angle calculation circuit 28 determines the presence/absence of the origin signal. The origin signal may be received from the origin detection circuit 32, or only the presence/absence of the origin signal may be received from the phase detection circuit 26.

In step S38, the angle calculation circuit 28 resets the rotational angle to zero.

Figure 19:
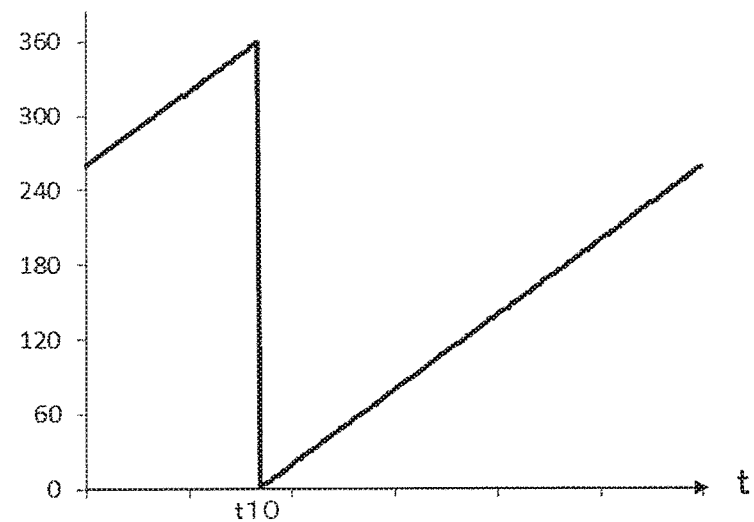
FIG. 19 A graph showing an example rotational angle of the rotor 20*a* calculated by the angle calculation circuit 28.

FIG. 19 shows the rotational angle of the rotor 20a calculated by the angle calculation circuit 28. The rotation is such that the difference of the initial phase $\theta 0$ is maintained between the rotational angle of the rotor 20a and the rotational angle of the substrate 10 for sample analysis. Therefore, the rotational angle of the substrate 10 for sample analysis can be determined from the rotational angle of the rotor 20a. In the present embodiment, since the initial phase $\theta 0$ is reset to zero, the rotational angle of the rotor 20a represents the rotational angle of the substrate 10 for sample analysis.

Through the processes described above, the sample analysis device 1 can determine the rotational angle of the rotor 20a.

Figure 20:
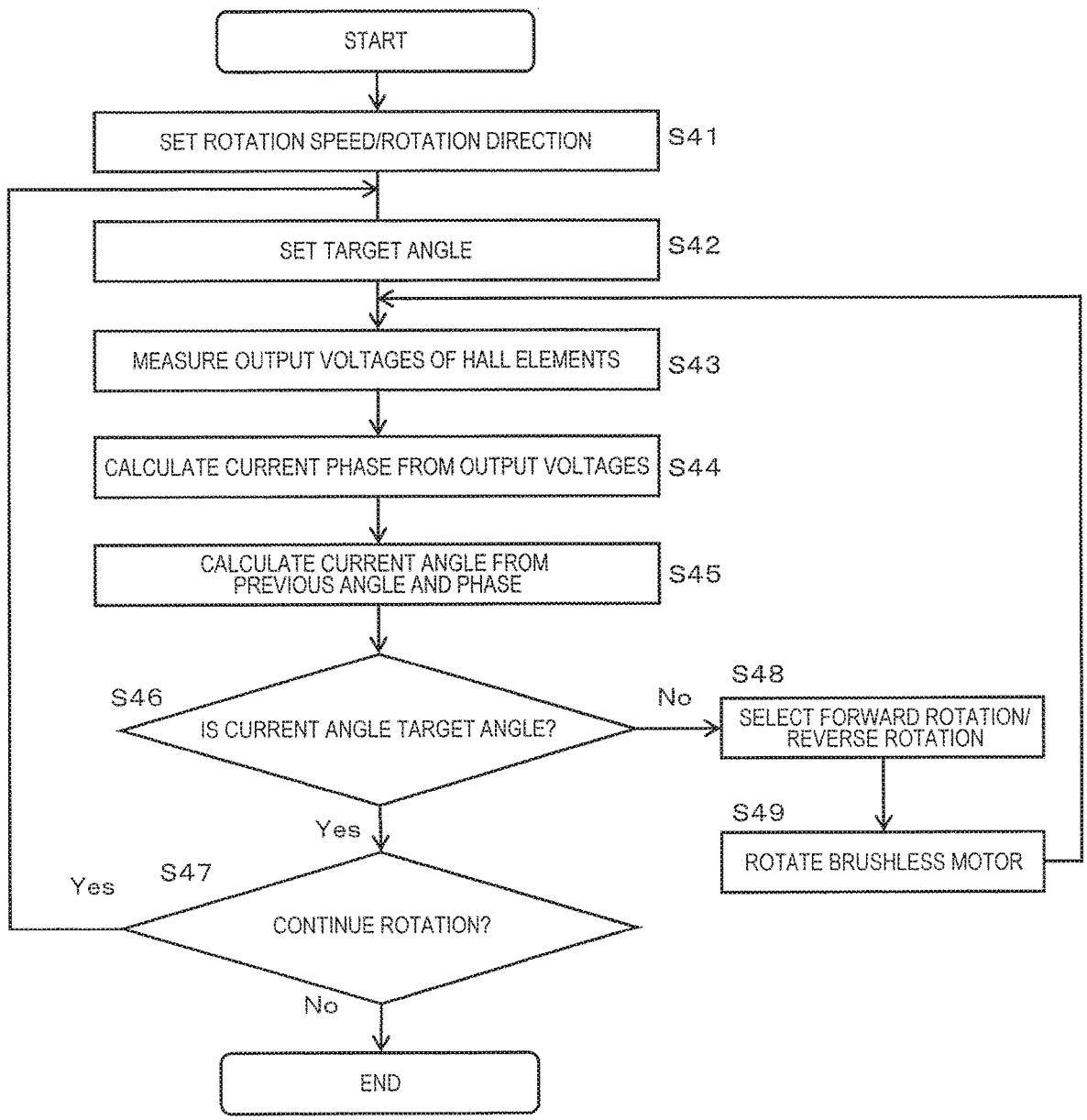
FIG. 20 A flow chart showing an example procedure for the process in which the substrate 10 for sample analysis is rotated by the sample analysis device 1.

FIG. 20 shows the procedure for the process in which the substrate 10 for sample analysis is rotated by the sample analysis device 1.

In step S41, the control circuit 30 sets a predetermined rotation speed and rotation direction for the substrate 10 for sample analysis, which has been set.

In step S42, the control circuit 30 sets a target angle.

In step S43, the phase detection circuit 26 measures the output voltages of the Hall elements H1 and H2.

In step S44, the phase detection circuit 26 calculates the current phase $\theta$ of the rotor 20a from the output voltages.

In step S45, the angle calculation circuit 28 calculates the current rotational angle of the rotor 20a by using the previously-measured rotational angle of the rotor 20a, the current phase $\theta$ of the rotor 20a calculated in step S44, and the previous phase of the rotor 20a. This process corresponds to the process of FIG. 17.

In step S46, the control circuit 30 determines whether or not the current angle of the rotor 20a is equal to the target angle. If the rotor 20a is located at the target angle, the process proceeds to step 47, and the process otherwise proceeds to step 48.

In step S47, the control circuit 30 determines whether or not to continue rotation. If rotation is to be continued, the process returns to step 42, and the process is ended if rotation is not to be continued.

In step S48, the control circuit 30 determines whether the brushless motor 20 is to be rotated in forward rotation or in reverse rotation.

In step S49, the driver circuit 22 rotates the brushless motor 20 in accordance with the determination of the control circuit 30.

Figure 21:
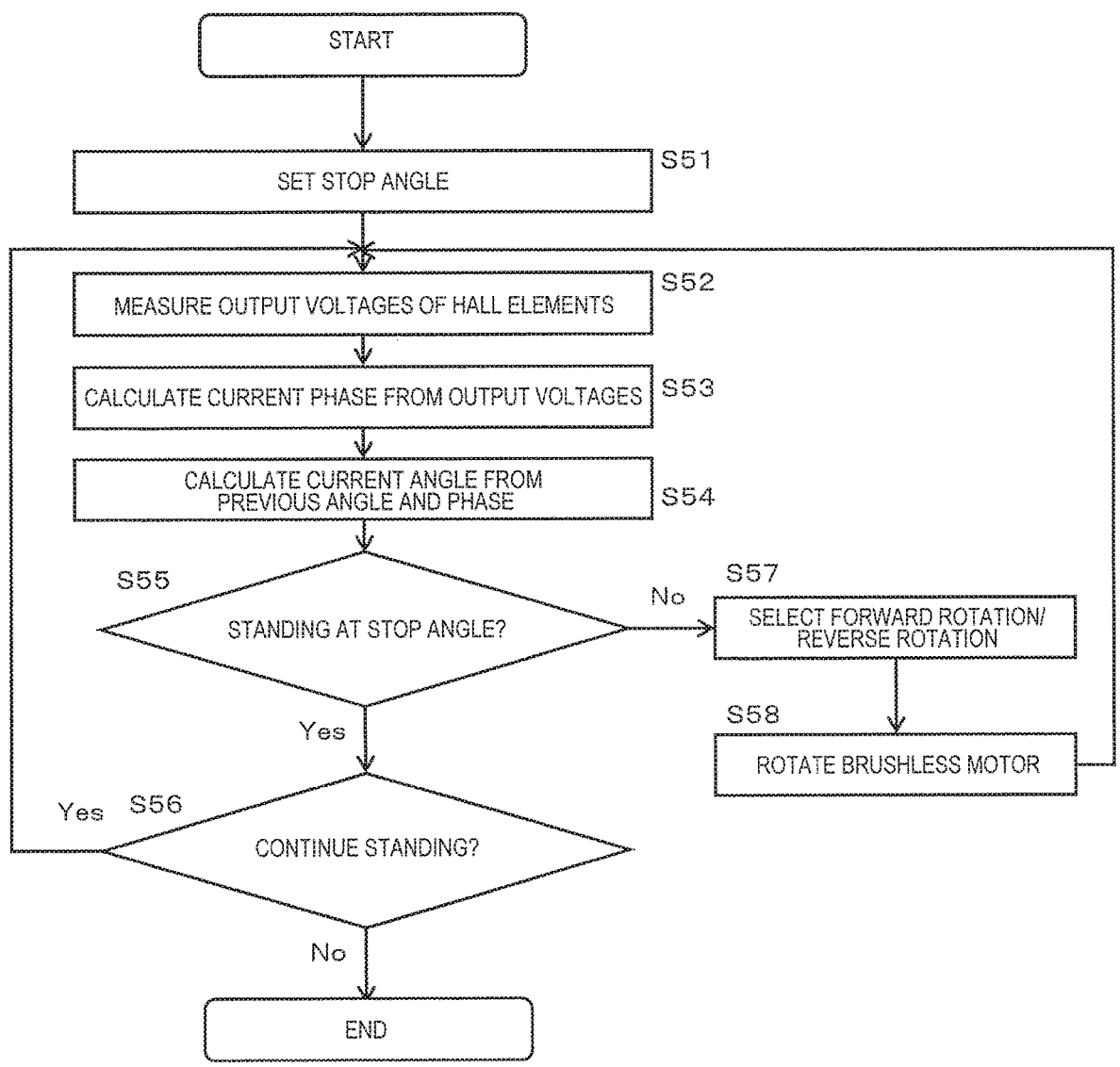
FIG. 21 A flow chart showing an example procedure for the operation in which the substrate 10 for sample analysis is stopped at a target angle by the sample analysis device 1.

FIG. 21 shows the procedure for the operation in which the substrate 10 for sample analysis is stopped at the target angle by the sample analysis device 1.

In step S51, the control circuit 30 sets a predetermined stop angle for the substrate 10 for sample analysis, which has been set.

In step S52, the phase detection circuit 26 measures the output voltages of the Hall elements H1 and H2.

In step S53, the phase detection circuit 26 calculates the current phase $\theta$ of the rotor 20a from the output voltages.

In step S54, the angle calculation circuit 28 calculates the current rotational angle of the rotor 20a by using the previously-measured rotational angle of the rotor 20a, the current phase $\theta$ of the rotor 20a calculated in step S44, and the previous phase of the rotor 20a. This process corresponds to the process of FIG. 17.

In step S55, the control circuit 30 determines whether or not the brushless motor 20 is standing at the target stop angle. If the brushless motor 20 is standing at the target angle, the process proceeds to step S56, and the process otherwise proceeds to step S57.

In step S56, the control circuit 30 determines whether or not to continue the standing state. If the standing state is to be continued, the process returns to step S52, and the process is ended if the standing state is not to be continued. The stopping control is assumed to be an operation of controlling the motor so that the disc is always at a fixed position even under an external force such as gravity. Therefore, the process of step S52 and subsequent steps is performed even if the standing state is to be continued.

In step S57, the control circuit 30 determines whether the brushless motor 20 is to be rotated in forward rotation or in reverse rotation.

In step S58, the driver circuit 22 rotates the brushless motor 20 in accordance with the determination of the control circuit 30.

A variation of the sample analysis device 1 according to the present embodiment will now be described. Note that those components having like configurations and/or like functions will be denoted by like reference numerals and will not be further described below.

Figure 22:
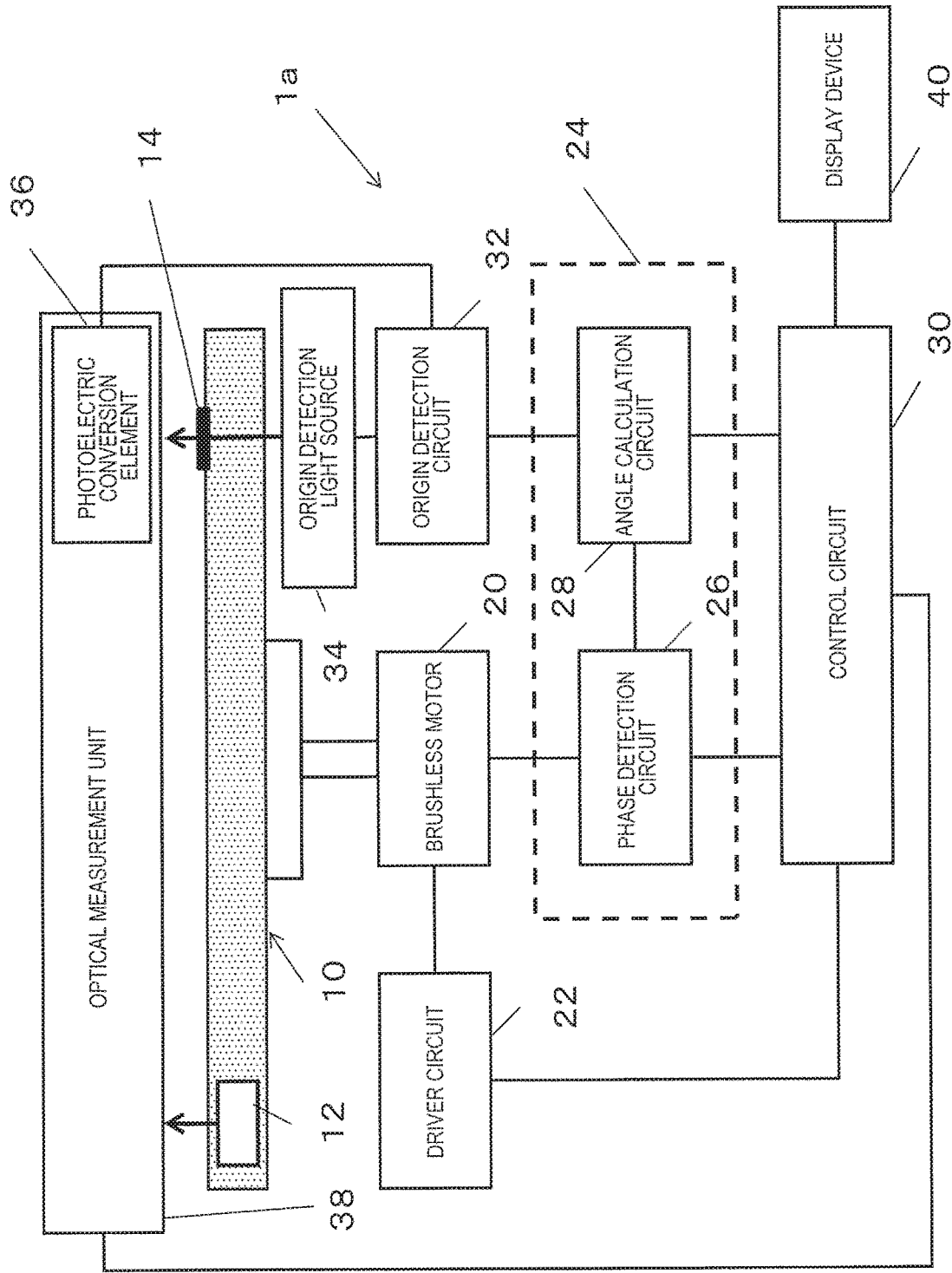
FIG. 22 A diagram showing an example configuration of a sample analysis device 1*a* according to a first variation of Embodiment 1.

FIG. 22 shows a configuration of a sample analysis device 1a according to the first variation of the present embodiment. A difference between the sample analysis device 1a and the sample analysis device 1 (FIG. 1) is that the photoelectric conversion element 36 of the sample analysis device 1a is used not only for origin detection but also for optical measurement for sample analysis. There is one photoelectric conversion element 36 provided in the optical measurement unit 38. The photoelectric conversion element 36 is first used in the origin detection process before starting the rotation of the substrate 10 for sample analysis, and is thereafter used in the angle calculation process performed by the angle calculation circuit 28, and in the process in which the optical measurement unit 38 detects light emission in the measurement chamber 12 while analyzing the sample.

The configuration described above is suitable for cases where the sample analysis device 1a is a device for detecting optical absorbance, turbidity or fluorescent emission.

Figure 23:
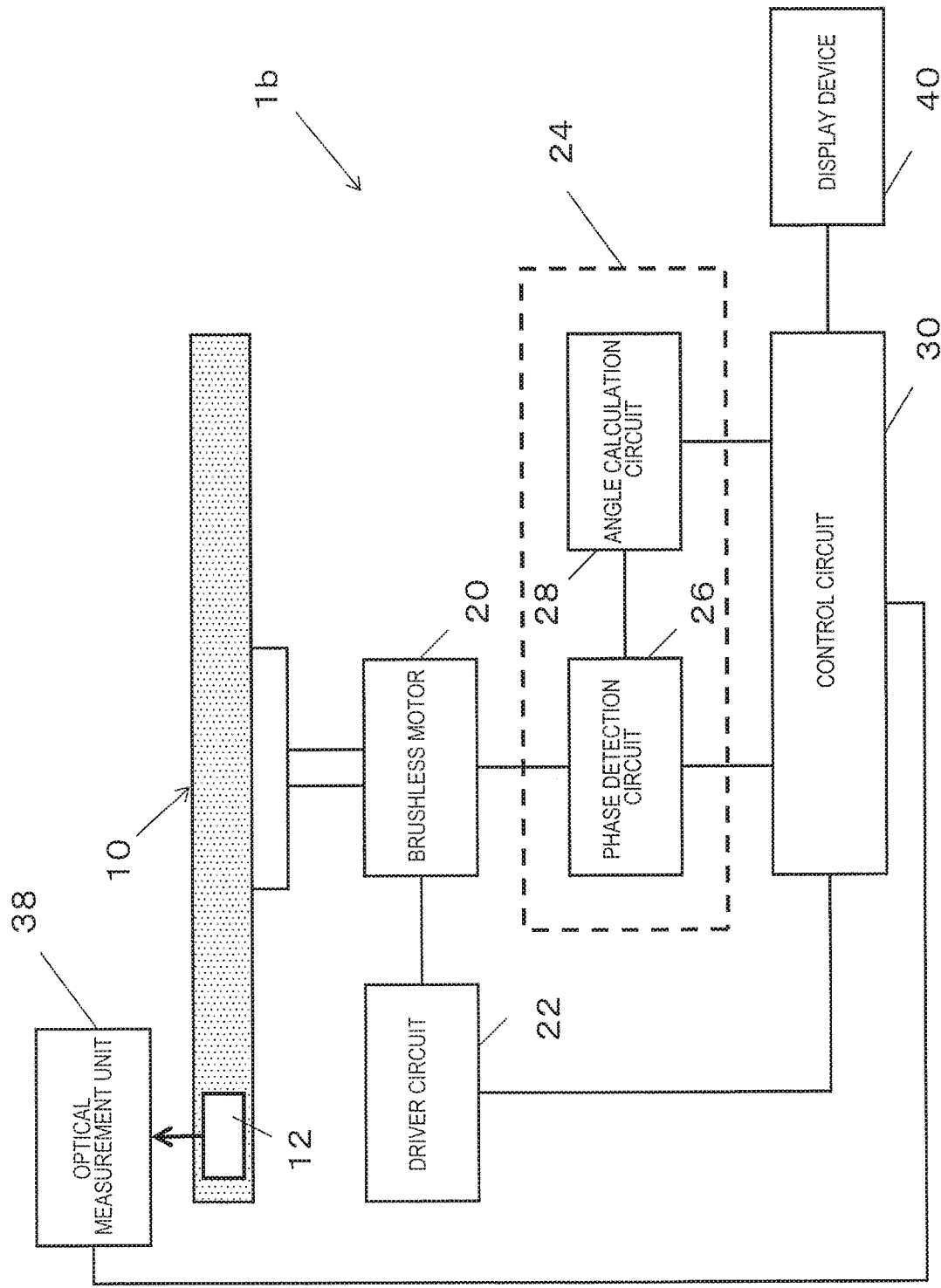
FIG. 23 A diagram showing an example configuration of a sample analysis device 1*b* according to a second variation of Embodiment 1.

FIG. 23 shows a configuration of a sample analysis device 1b according to the second variation of the present embodiment.

A difference between the sample analysis device 1b and the sample analysis device 1 (FIG. 1) is that there is no element for origin detection in the sample analysis device 1b. Specifically, the origin detection circuit 32, the origin detection light source 34 and the photoelectric conversion element 36, which are provided in the sample analysis device 1 (FIG. 1), are absent in the sample analysis device 1b. Note that while the photoelectric conversion element 36 for detecting light from the origin detection light source 34 is omitted in the sample analysis device 1b, a photoelectric conversion element (not shown) may be provided in the optical measurement unit 38.

As a condition for omitting an element for origin detection, it is necessary that the rotor of the brushless motor 20 of the sample analysis device 1b is 2-pole. This is because if the rotor has 2-pole, it is possible to determine the current position of the rotor from the output voltage waveforms of the Hall elements H1 and H2. More specifically, if the rotor has 2-pole, one rotation of the rotor corresponds to one cycle of the output voltage waveforms of the Hall elements H1 and H2 (FIG. 11). By looking at the output voltage waveforms of the Hall elements H1 and H2, it is possible to determine the current position of the north pole or the south pole of the rotor, in other words, the angle of the rotor. This eliminates the need for the origin detection process, and it is possible to omit the element for origin detection.

Note that in conjunction with the sample analysis device 1 (FIG. 1), FIG. 3 to FIG. 7 illustrate a configuration in which the brushless motor 20 is 2-pole, for example. Note that even if the brushless motor 20 is 2-pole, the origin detection process may be performed.

It is assumed in the embodiment described above that the arc tangent is calculated by a digital process. However, it does not always need to be done by a digital process, and the arc tangent may be calculated by an analog signal process, for example.

The principle of the calculation is as follows. In an equation in which the arc tangent is expressed by $\tan^{-1}(x)$, it can be represented by a Taylor series equation if the absolute value of x is less than 1. In order to calculate the $(2n+1)^{th}$-order term of the Taylor series, a circuit is configured to calculate the logarithm of x, multiply it by $(2n+1)$ and calculate the antilogarithm thereof. A well-known logarithm conversion circuit may be used in order to calculate the logarithm of x. A well-known antilogarithm conversion circuit may be used in order to calculate the antilogarithm.

Calculation using a Taylor series can be done by using a number of sets of these circuits, equal to the number of orders needed for a calculation precision, arranged in parallel, and by finally adding the results together. Note that where a logarithm is calculated, if x<0, it is necessary to convert the value to −x so as to eventually correct the calculation result.

Embodiment 2

Embodiment 1 is directed to the sample analysis devices 1, 1a and 1b each including a brushless motor with a 2-pole rotor 20a and 3-phase 3-slot coils 20b.

The present embodiment is directed to a sample analysis device including a brushless motor having a 2n-pole (n: an integer of 2 or more) rotor and a 3-phase 3m-slot (m: an integer of 1 or more).

First, the hardware configuration of the sample analysis device of the present embodiment is substantially the same as that of FIG. 1, except for the configuration of the brushless motor 20, and connections and signal processing systems arising from the configuration. Therefore, the operation of the sample analysis device will be described also in the present embodiment by using the same reference numerals as those of the sample analysis device 1 of Embodiment 1.

Note however that the sample analysis device 1 will be described as having a brushless motor 21 with a 2n-pole (n: an integer of 2 or more) rotor and a 3-phase, 3m-slot (m: an integer of 1 or more), instead of the brushless motor 20.

Figure 24:
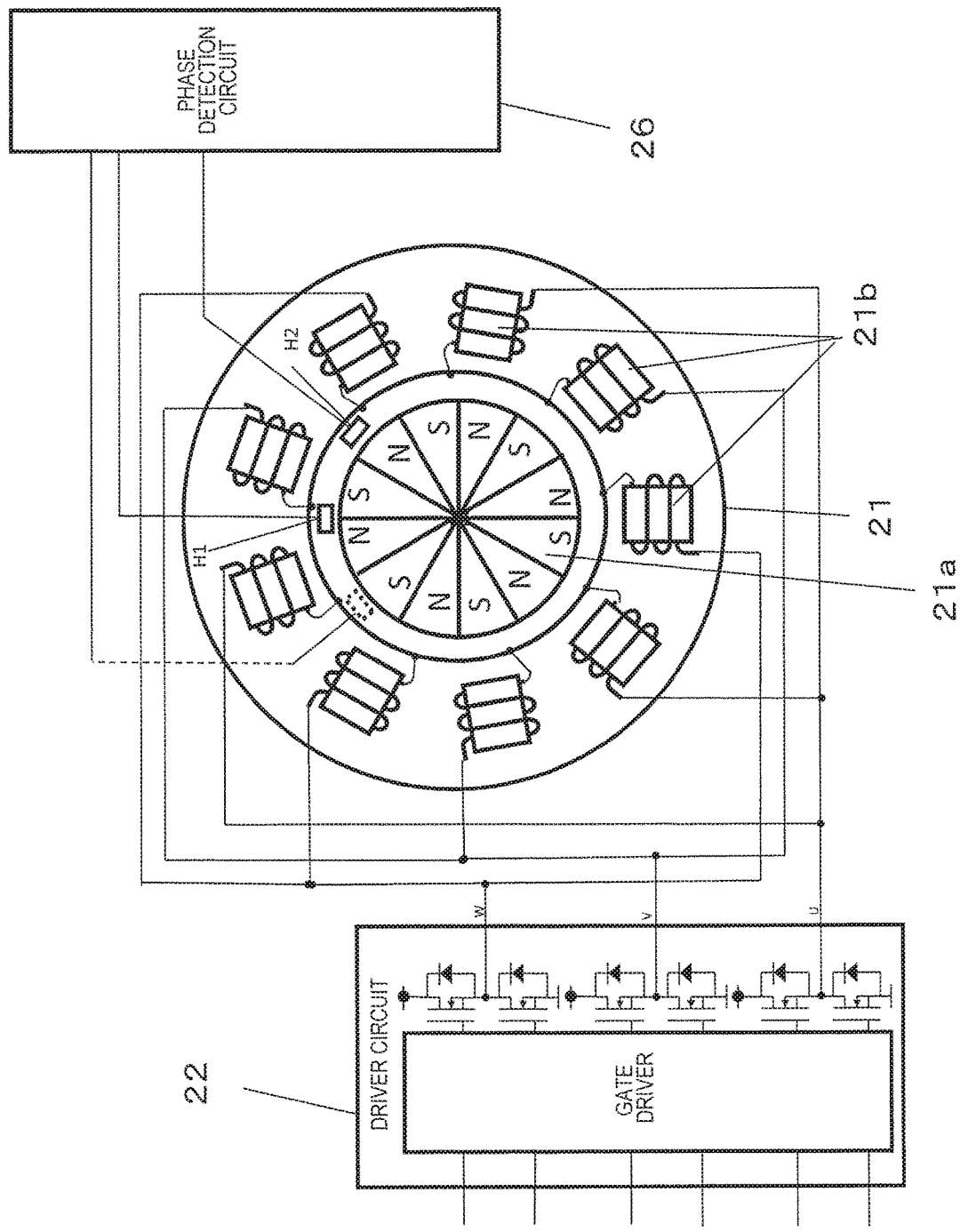
FIG. 24 A diagram showing an example configuration of a brushless motor 21 and the driver circuit 22 according to Embodiment 2, and an example connection relationship between the brushless motor 21, the driver circuit 22 and the phase detection circuit 26.

FIG. 24 shows an example configuration of the brushless motor 21 and the driver circuit 22 according to the present embodiment, and a connection relationship between the brushless motor 21, the driver circuit 22 and the phase detection circuit 26. FIG. 24 corresponds to the configuration of FIG. 3 relating to Embodiment 1.

The brushless motor 21 includes a 2n-pole (n: an integer of 2 or more) rotor 21a and 3-phase, 3m-slot (m: an integer of 1 or more) coils 21b. In the present embodiment, the rotor 21a is 12-pole (n=6) and the coils 21b are 3-phase, 9-slot (m=3). The three coils 21b are provided respectively as the U, V and W phase.

Based on instructions from the control circuit 30 to be received from the left side of the figure, the driver circuit 22 controls the rotation direction, the rotation speed, etc., of the brushless motor 21 by adjusting the direction and the level of the current flow through each of the three coils 21b corresponding respectively to the U, V and W phase. The three coils 21b of the different phases are connected in parallel to the driver circuit 22. The operation of the driver circuit 22 is the same as that of Embodiment 1, except that the ON, OFF and reverse periods are 1/n times those of Embodiment 1.

At least two Hall elements H1 and H2 are provided in the brushless motor 21. In the present embodiment, the Hall elements H1 and H2 are arranged in a positional relationship of the angle α (0°<α<180°) from each other with respect to the rotation axis of the rotor 21a. In the present embodiment, the angle α=−40°.

Where the brushless motor 21 of the present embodiment is used, the phase ωt is obtained as the inverse tangent (arc tangent) of (sin ωt/cos ωt). This is similar to Embodiment 1, and the formula is also the same. The basis for this is as follows.

Figure 25:
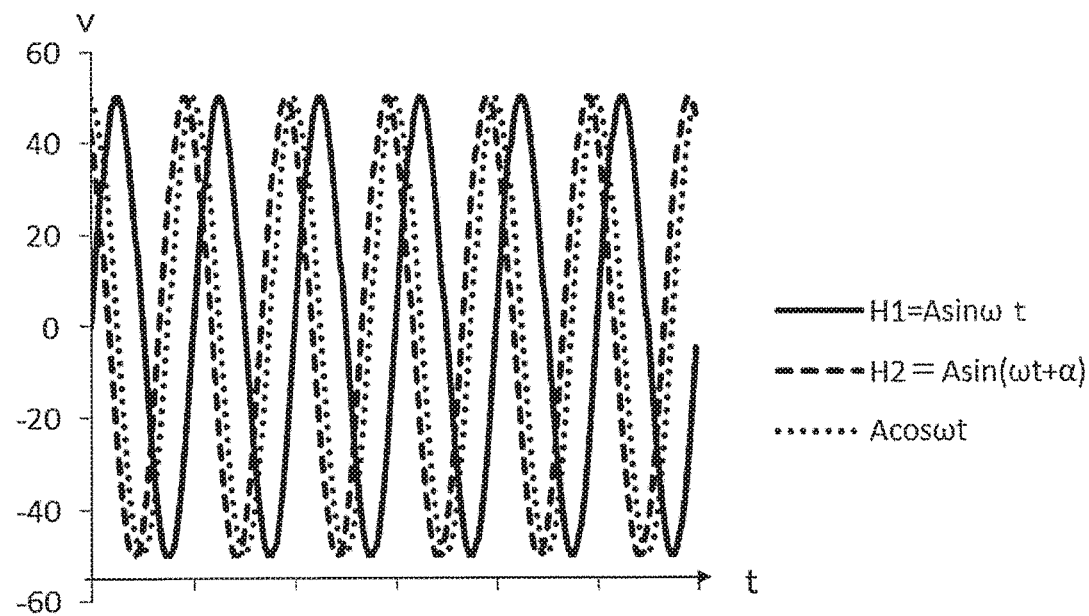
FIG. 25 A graph showing example voltage signal waveforms of the Hall elements H1 and H2.

FIG. 25 shows example voltage signal waveforms of the Hall elements H1 and H2. FIG. 25 shows the voltage signal waveforms of the Hall elements H1 and H2. The waveform of cos ωt is also shown. FIG. 25 corresponds to the waveform of FIG. 12 relating to Embodiment 1.

As shown in FIG. 25, with the brushless motor 21 of the present embodiment, six cycles of output voltage signals of the Hall elements H1 and H2 are output for one rotation.

Now, if the angular difference between the Hall elements H1 and H2 installed is expressed as −40°, the output voltage signals of the Hall elements H1 and H2 transition for one cycle for every 60° rotation of the brushless motor 21. Since the angular difference arising from the arrangement of the Hall elements H1 and H2 is −40°, the phase difference between the output voltage signals is calculated to be 360/60×(−40)=−240°. A −240° phase difference is equal to a 120° phase difference, and it is equal to the phase difference of 120° in Embodiment 1. That is, it is possible to obtain the phase at based on Equation 1 explained in Embodiment 1 as described above.

For this, the waveform of cost is also needed. The phase detection circuit 26 calculates the waveform of cost shown in FIG. 25 by the equation on the fourth line of Equation 1.

Figure 26:
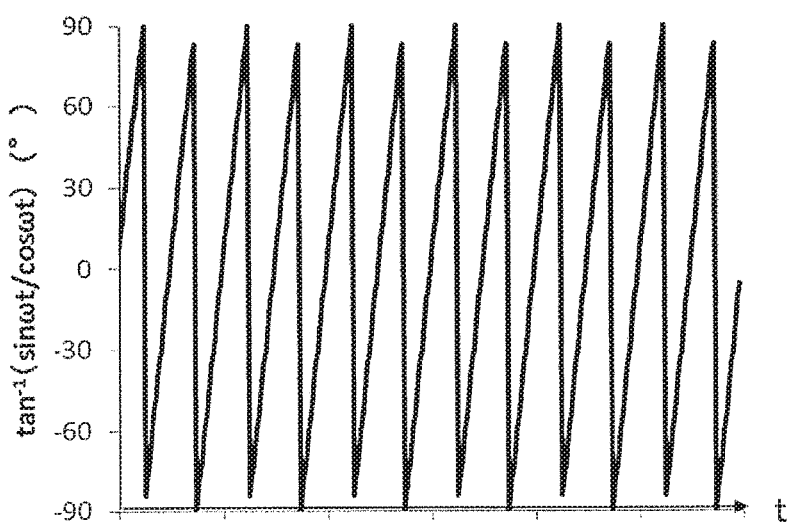
FIG. 26 A graph showing an example waveform of $\tan^{-1}(\sin \omega t/\cos \omega t)$ calculated by the phase detection circuit 26.

FIG. 26 shows the waveform of $\tan^{-1}(\sin \omega t/\cos \omega t)$ calculated by the phase detection circuit 26. FIG. 26 corresponds to the waveform of FIG. 14 relating to Embodiment 1. Note however that with the configuration of the present embodiment, since the cycle is ⅙, the obtained waveform is compressed 6 times in the time direction.

Figure 27:
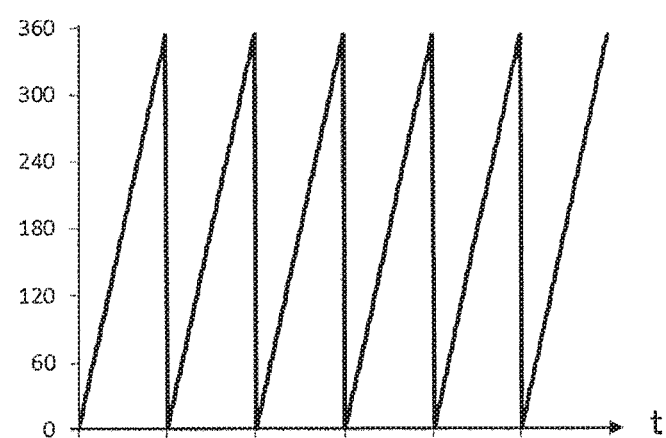
FIG. 27 A graph showing an example phase of a rotor 21*a* calculated by the phase detection circuit 26.

FIG. 27 shows the phase of the rotor 21a calculated by the phase detection circuit 26. The phase of the rotor 21a can be obtained by a process similar to the process shown in FIG. 13.

The horizontal axis of FIG. 27 represents time, and it is of the same scale as the horizontal axis of FIG. 15. A comparison between the phase of FIG. 27 and the phase of FIG. 15 shows that a phase of one cycle (360°) is obtained for one rotation of the rotor 21a of Embodiment 1 shown in FIG. 19, whereas a phase of six cycles is obtained for one rotation of the rotor 21a of the present embodiment.

Figure 28:
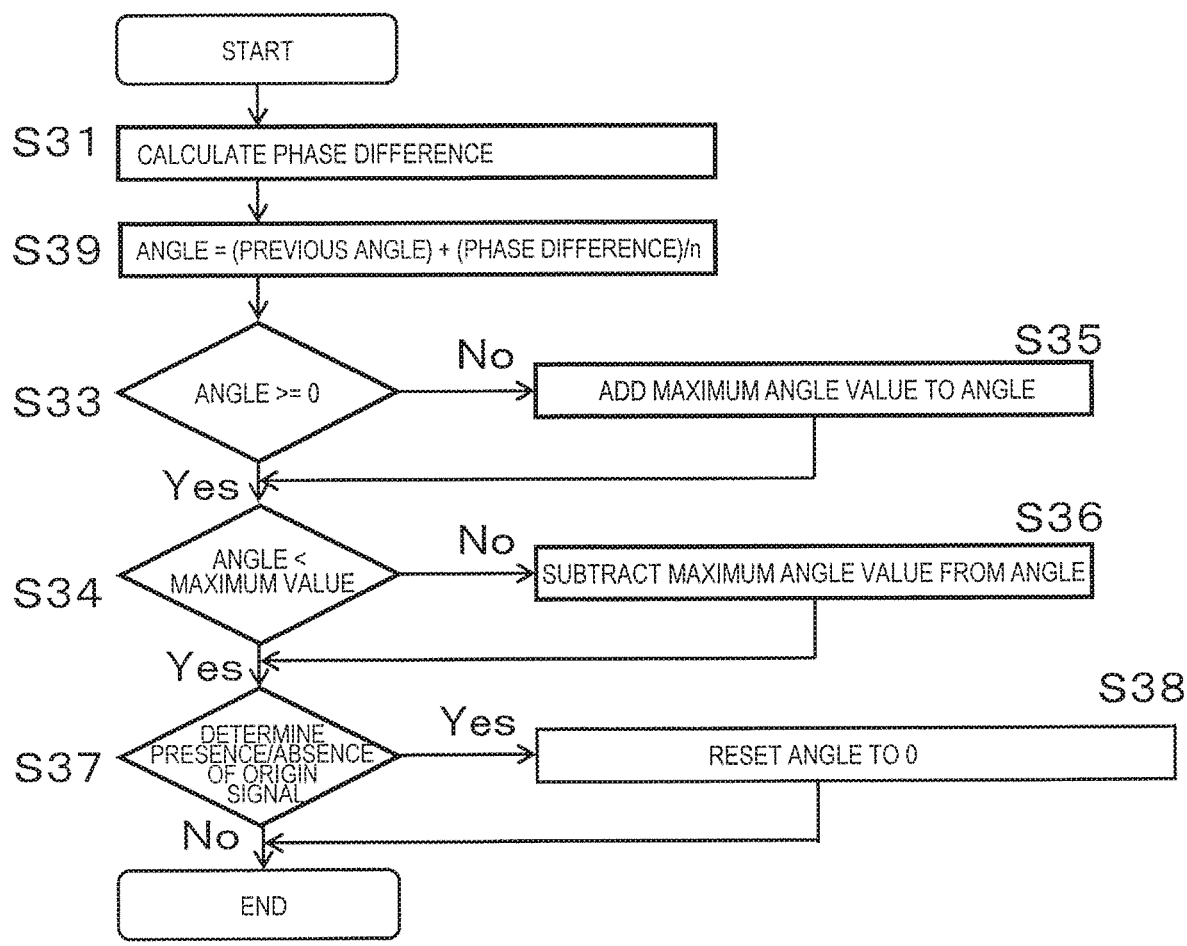
FIG. 28 A flow chart showing an example procedure for the process of the angle calculation circuit 28.

FIG. 28 shows the procedure for the process of the angle calculation circuit 28. The angle calculation circuit 28 can detect the rotational angle of the rotor 21a, by the procedure shown in the figure, by using the phase of the rotor 21a.

A difference between the process procedure shown in FIG. 28 and the process procedure shown in FIG. 17 is that step S39 is provided instead of step S32 of FIG. 17. In step S39, the phase difference is divided by n. This is because the phase difference value corresponds to a scale that is 1/n times the phase of Embodiment 1. The other processes, which are the same as those of FIG. 17, are denoted by like reference numerals and will not be further described below.

Figure 29:
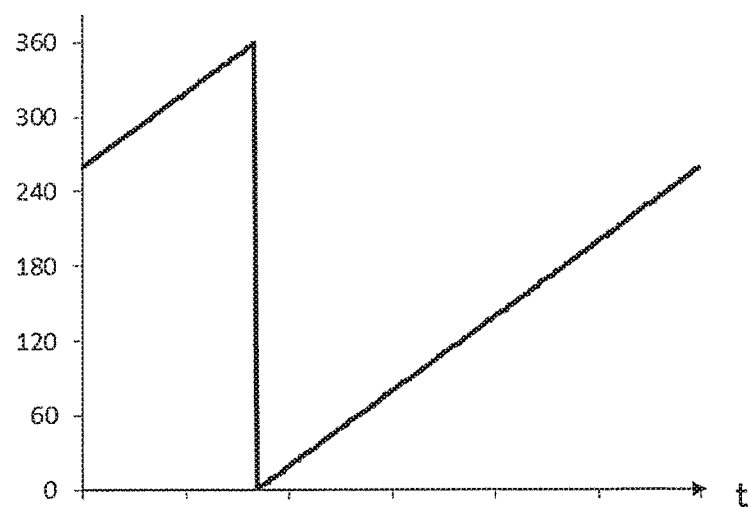
FIG. 29 A graph showing an example rotational angle of the rotor 21*a* calculated by the angle calculation circuit 28 according to Embodiment 2.

FIG. 29 shows the rotational angle of the rotor 21a calculated by the angle calculation circuit 28 according to the present embodiment. FIG. 29 corresponds to the waveform of FIG. 19 relating to Embodiment 1. Note that they are the same. The reason is that the rotational angle as the brushless motor 21 remains the same irrespective of the number of poles of the rotor 21a.

The second embodiment has been described above. In the present embodiment, it has been demonstrated that calculations based on the same Equation 1 can be used even if the number of poles and the number of slots of the brushless motor are not 2-pole, and 3-slot. It is understood that processes may be changed according to the number of poles of the rotor 21a, the number of slots of the brushless motor 21, and the positional relationship (angle) between at least two Hall elements.

Note that Embodiment 1 and the present embodiment differ from each other only for the configuration of the brushless motor. Therefore, Variations 1 and 2 (FIG. 22 and FIG. 23) of Embodiment 1 can be used as variations of the present embodiment by changing the configuration of the brushless motor.

Embodiment 3

It is assumed in the embodiment described above that noise is not contained in the output voltage waveforms of the Hall elements H1 and H2.

However, there may be situations where noise f(t) is superimposed, with similar conditions, on both of the output voltage waveforms of the Hall elements H1 and H2. In the present embodiment, the process of detecting the rotational angle in such a situation will be described. As a conclusion, the phase at to be determined can be obtained as the arc tangent of (sin ωt/cos ωt), as in Equation 1.

It is assumed that the configuration of the sample analysis device of the present embodiment is the same as that of the sample analysis device 1 of Embodiment 2.

Figure 30:
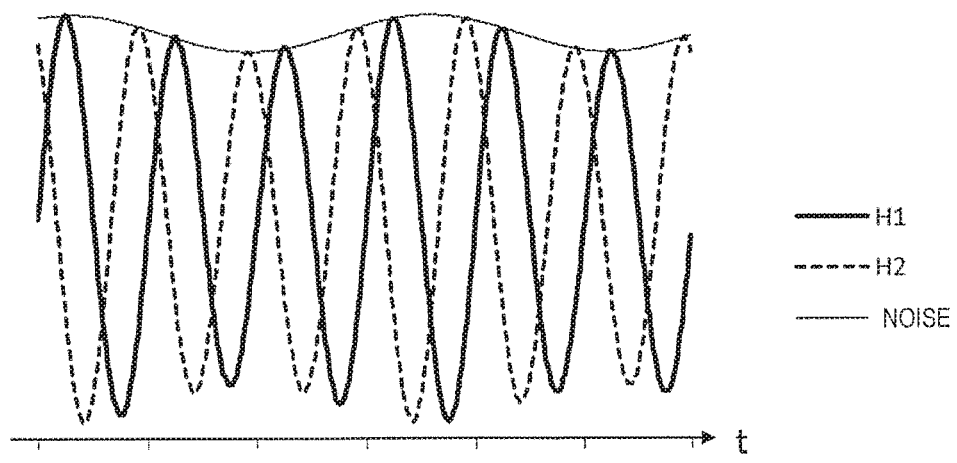
FIG. 30 A graph showing an example of output voltage waveforms of the Hall elements H1 and H2 with noise superimposed thereon.

FIG. 30 shows the output voltage waveforms of the Hall elements H1 and H2 with noise superimposed thereon. Compared with the waveform example of FIG. 25, the output voltage waveforms both fluctuate due to the influence of noise. The factor for the fluctuation of the output voltage waveforms may be, for example, a situation where the magnetic force of the rotor 21a of the brushless motor 21 varies locally.

$$H_1 = f(t)\sin\omega t \qquad [\text{Equation 2}]$$
$$H_2 = f(t)\sin(\omega t + \alpha)$$
$$\quad = f(t)(\sin\omega t\cos\alpha + \cos\omega t\sin\alpha)$$
$$f(t)\cos\omega t = \frac{H_2 - H_1\cos\alpha}{\sin\alpha}$$
$$\tan^{-1}\frac{\sin\omega t}{\cos\omega t} = \tan^{-1}\frac{f(t)\sin\omega t}{f(t)\cos\omega t}$$
$$\quad = \tan^{-1}\frac{H_1 \times \sin\alpha}{H_2 - H_1\cos\alpha}$$

In Equation 2, the output voltage waveforms of the Hall elements H1 and H2 are multiplied by the same noise component f(t). However, the noise component f(t) does not appear in the equation for calculating the arc tangent of (sin ωt/cos ωt). That is, it is demonstrated that even if the output voltage waveforms of the Hall elements H1 and H2 vary due to the influence of a common noise component, it is possible to derive the phase by the same formula as Equation 1 using the output voltages and the installment angle α.

Figure 31:
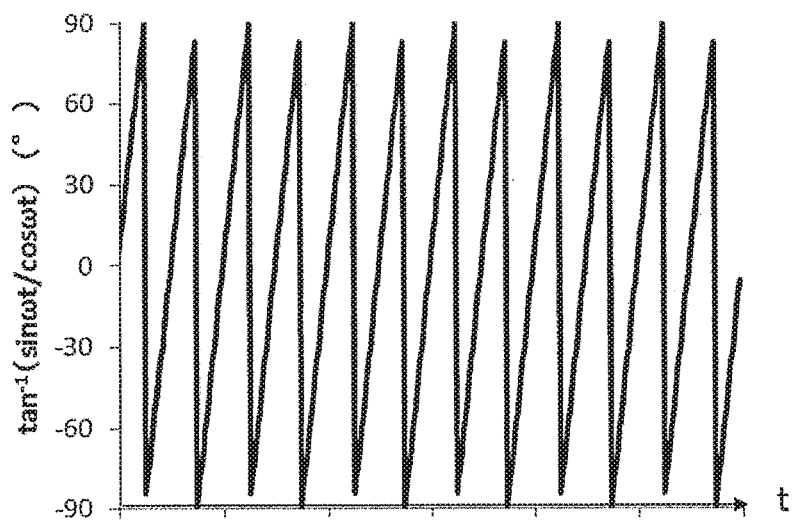
FIG. 31 A graph showing an example phase waveform detected by the phase detection circuit 26.

The present inventors actually obtained the phase at using the phase detection circuit 26. FIG. 31 shows the phase waveform detected by the phase detection circuit 26. This waveform is equal to the phase waveform (FIG. 26), which is obtained without taking the influence of noise into consideration.

As a result, the calculation process for the rotational angle of the rotor 21a is totally the same as the calculation process described above in Embodiment 2. Note that the description thereof is omitted.

The present embodiment has been described separately from Embodiments 1 and 2. However, it can be said that it does not need to be implemented as a separate embodiment after all if a common noise component is superimposed on the output voltage waveforms of the Hall elements H1 and H2.

Embodiment 4

The present embodiment is directed to a phase detection process when there is a sensitivity difference between the Hall elements H1 and H2.

Figure 32:
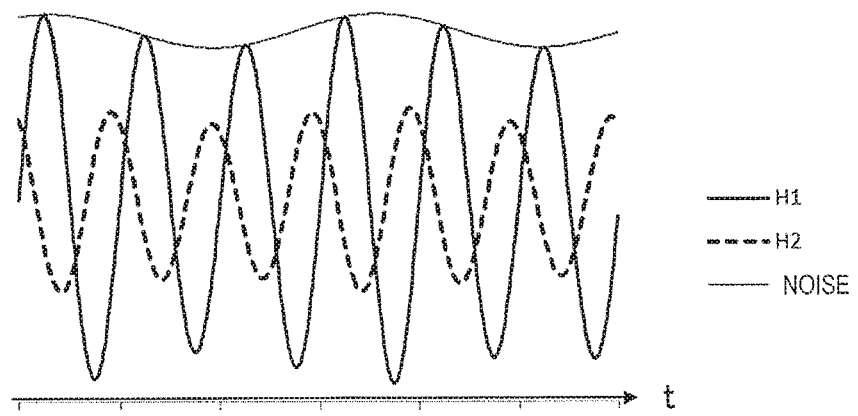
FIG. 32 A graph showing an example of output voltage waveforms of the Hall elements H1 and H2 with a sensitivity difference therebetween assumed in Embodiment 3.

FIG. 32 shows an example of the output voltage waveforms of the Hall elements H1 and H2 with a sensitivity difference therebetween assumed in the present embodiment. A sensitivity difference can be said to be an individual difference that exists in the first place between the Hall elements H1 and H2, or can be said to be an individual difference that develops through changes over time. The former individual difference can be specified at the shipment of the brushless motor or at the shipment of the sample analysis device. On the other hand, the latter individual difference develops through changes over time of the sample analysis device, and it is difficult to specify the latter individual difference at the shipment of the sample analysis device.

The sensitivity difference between the output voltage waveforms of the Hall elements H1 and H2 shown in FIG. 32, assuming that they change in the same phase, can be represented by a ratio of β (one of them being 1) (β will hereinafter be referred to as the "sensitivity ratio"). That is, using the sensitivity ratio β, H1 and H2 can be expressed as shown in Equation 3 below. The sensitivity ratio β also appears in the equation for obtaining the arc tangent of (sin ωt/cos ωt).

$$H_1 = f(t)\sin\omega t \quad \text{[Equation 3]}$$

$$H_2 = \beta f(t)\sin(\omega t + \alpha)$$
$$= \beta f(t)(\sin\omega t \cos\alpha + \cos\omega t \sin\alpha)$$

$$f(t)\cos\omega t = \frac{\frac{H_2}{\beta} - H_1 \cos\alpha}{\sin\alpha}$$

$$\tan^{-1}\frac{\sin\omega t}{\cos\omega t} = \tan^{-1}\frac{f(t)\sin\omega t}{f(t)\cos\omega t}$$
$$= \tan^{-1}\frac{H_1 \times \sin\alpha}{\frac{H_2}{\beta} - H_1 \cos\alpha}$$

That is, if the sensitivity ratio β is determined, the phase of the rotor can be detected even if there is a sensitivity difference between the Hall elements H1 and H2.

Note that even if a sensitivity difference develops through changes over time, it is easy to determine the sensitivity ratio β. When a rotor is rotated, the Hall elements H1 and H2 detect the magnetic force of the common rotor. Therefore, even though there is a phase difference arising from the positional relationship, the output voltage waveforms of the Hall elements H1 and H2 are supposed to be the same. In view of this, the output voltage waveforms of the Hall elements H1 and H2 may be measured at the start of operation of the sample analysis device, the ratio therebetween can be obtained as the sensitivity ratio β. The sample analysis device may perform this operation at the start of initialization immediately after power-up, thereby obtaining the sensitivity ratio β. Then, it is possible to detect the phase of the rotor based on Equation 3 in a subsequent process.

Figure 33:
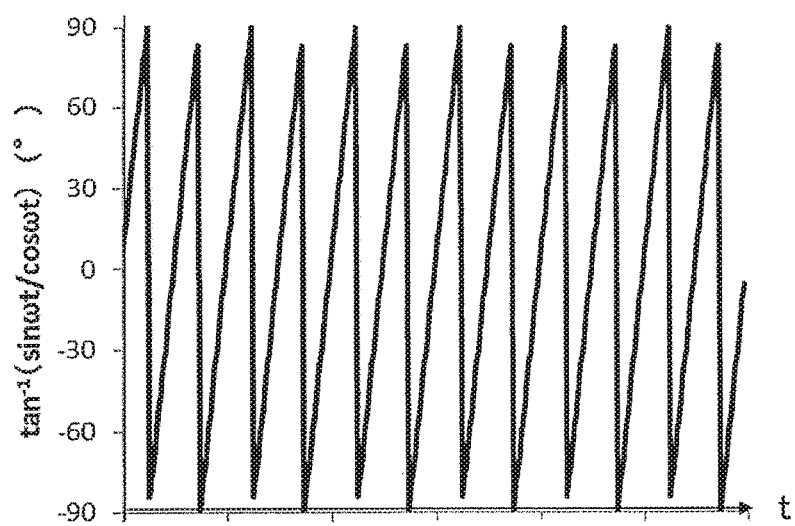
FIG. 33 A graph showing an example phase waveform detected by a process according to Embodiment 4.

The present inventors actually obtained the phase ωt using the phase detection circuit. FIG. 33 shows a phase waveform obtained by correcting the sensitivity difference between Hall elements. If the sensitivity difference between Hall elements shown in Embodiments 1 to 3 is the same, the same waveform as that of FIG. 26 is obtained. Even if there is a sensitivity difference between Hall elements, it can be corrected using β of Equation 3, thereby obtaining the same waveform as that shown in FIG. 26.

Note that the phase detection principle of the present embodiment is applicable to any of the sample analysis devices of Embodiments 1 to 3.

INDUSTRIAL APPLICABILITY

The present disclosure can be used as a technique for use in a sample analysis device having a brushless motor for obtaining the rotational angle of the brushless motor. The present disclosure can be used, for example, as a detection circuit for obtaining the rotational angle of a brushless motor, a sample analysis device provided with a detection circuit and a brushless motor, and a computer program for operating such a sample analysis device.

REFERENCE SIGNS LIST 1 sample analysis device
20, 21 Brushless motor
20a, 21a Rotor
20b, 21b Coil
22 Driver circuit
24 Rotational angle detection circuit
30 control circuit
32 Origin detection circuit
34 Origin detection light source
36 Photoelectric conversion element
38 Optical measurement unit
40 Display device
H1, H2 Hall element

The invention claimed is:
1. A sample analysis device for transferring and analyzing a liquid in a substrate for sample analysis loaded therein by rotating the substrate for sample analysis, wherein a marker given a predetermined physical characteristic is provided at a predetermined position on the substrate for sample analysis, the sample analysis device comprising:
a brushless motor;
a rotational angle detection circuit that detects a rotational angle of the brushless motor; and
an origin detection circuit that detects a position of the marker by detecting the predetermined physical characteristic and determines the position of the marker to be an origin position, wherein:
the brushless motor includes:
a 2n-pole (n: an integer of 1 or more) rotor; and
a first Hall element and a second Hall element arranged at a positional relationship of an angle α (0°<α<180°) from each other with respect to a rotation axis of the rotor, the first Hall element and the second Hall element each outputting a voltage signal in accordance with a magnitude of a magnetic field of the rotor,
the rotational angle detection circuit comprising:
a phase detection circuit that receives the voltage signals output respectively from the first Hall element and the second Hall element and that detects a phase of the rotor by using values of the voltage signals and information of the angle α; and
an angle calculation circuit that sets a predetermined reference angle based on the origin position detected by the origin detection circuit, and that calculates a rotational angle of the rotor calculated from an initial angle of the rotor based on the phase detected by the phase detection circuit and the predetermined reference angle,
wherein:
when the voltage signal of the first Hall element is denoted as H1=A sin ωt and the voltage signal of the second Hall element is denoted as H2=A sin(ωt+α), or
when the voltage signal of the first Hall element is denoted as H1=f(t)A sin ωt and the voltage signal of the second Hall element is denoted as H2=f(t)A sin(ωt+α), and a function f(t) is a noise component which is commonly superimposed on the first Hall element and the second Hall element,
the phase detection circuit configured to detect a phase θ of the rotor by calculating:

θ=tan⁻¹(H1·sin α)/(H2−H1·cos α), and wherein:
at a first point in time, the phase detection circuit detects a first phase of the rotor; and the angle calculation circuit calculates a first rotational angle of the rotor from the initial angle of the rotor based on the first phase and the predetermined reference angle, and further updates the predetermined reference angle to the first phase; and
at a second point in time different from the first point in time, the phase detection circuit detects a second phase of the rotor; and the angle calculation circuit calculates a rotational angle of the rotor from the predetermined reference angle based on the first rotational angle, the second phase and the updated predetermined reference angle.

2. The sample analysis device according to claim 1, wherein an initial value of the predetermined reference angle is 0°.

3. The sample analysis device according to claim 1, wherein:
when the rotor has 2n-pole (n: an integer of 2 or more), the angle calculation circuit receives, as an initial value of the predetermined reference angle, information for determining the initial angle of the rotor.

4. The sample analysis device according to claim 1, wherein:
when the rotor has 2n-pole (n=1),
the angle calculation circuit calculates a second rotational angle calculated from the initial angle of the rotor by adding together a difference value between the second phase and the updated predetermined reference angle and the first rotational angle.

5. The sample analysis device according to claim 1, wherein:
when the rotor has 2n-pole (n: an integer of 2 or more), the angle calculation circuit calculates a second rotational angle calculated from the initial angle of the rotor by adding together a value, which is obtained by dividing by n a difference value between the second phase and the updated predetermined reference angle, and the first rotational angle.

6. The sample analysis device according to claim 1, wherein the phase detection circuit detects a phase of the rotor by using a ratio between values of the voltage signals and information of the angle α.

7. The sample analysis device according to claim 1, wherein:
when sensitivities of the first Hall element and the second Hall element are different from each other for a magnetic field of the same magnitude, and a sensitivity ratio therebetween is denoted as β,
the phase detection circuit detects a phase of the rotor by using the sensitivity ratio β, a ratio between values of the voltage signals and information of the angle α.

8. The sample analysis device according to claim 1, wherein:
when the voltage signal of the first Hall element is denoted as H1=f(t)A sin ωt and the voltage signal of the second Hall element is denoted as H2=βf(t)A sin(ωt+α), and a function f(t) is a noise component which is commonly superimposed on the first Hall element and the second Hall element,
the phase detection circuit detects a phase θ of the rotor by calculating:

$$\theta = \tan^{-1}(H1 \cdot \sin \alpha)/(H2/\beta - H1 \cdot \cos \alpha).$$

9. A sample analysis device capable of transferring and analyzing a liquid in a substrate for sample analysis loaded therein by rotating the substrate for sample analysis, the sample analysis device comprising:
a brushless motor that rotates the substrate for sample analysis, the brushless motor including a 2n-pole (n=1) rotor and a first Hall element and a second Hall element arranged at an angle α (0°<α<180°) from each other with respect to a rotation axis of the rotor, the first Hall element and the second Hall element each outputting a voltage signal in accordance with a magnitude of a magnetic field of the rotor;
a driver circuit that drives the brushless motor; and
the rotational angle detection circuit according to claim 1 for detecting a rotational angle of the brushless motor.

10. The sample analysis device according claim 9, wherein the driver circuit stops rotation of the brushless motor based on the rotational angle of the brushless motor detected by the rotational angle detection circuit.

11. A sample analysis device for transferring and analyzing a liquid in a substrate for sample analysis loaded therein by rotating the substrate for sample analysis, wherein:
a marker given a predetermined physical characteristic is provided at a predetermined position on the substrate for sample analysis,
the sample analysis device comprising:
a brushless motor that rotates the substrate for sample analysis, the brushless motor including a 2n-pole (n: an integer of 1 or more) rotor and a first Hall element and a second Hall element arranged at an angle α (0°<α<180°) from each other with respect to a rotation axis of the rotor, the first Hall element and the second Hall element each outputting a voltage signal in accordance with a magnetic field of the rotor;
a driver circuit that controls how the brushless motor is driven;
an origin detection circuit that detects a position of the marker by detecting the predetermined physical characteristic and determines the position of the marker to be an origin position; and
the rotational angle detection circuit according to claim 1 that detects a rotational angle of the brushless motor, wherein:
a phase detection circuit of the rotational angle detection circuit detects a phase of the rotor at a point in time when the origin position is detected by the origin detection circuit; and
an angle calculation circuit of the rotational angle detection circuit sets, as the predetermined reference angle, a phase of the rotor at the point in time and calculates a rotational angle of the rotor from the predetermined reference angle based on the phase detected by the phase detection circuit and the predetermined reference angle.

12. The sample analysis device according to claim 11, wherein:
the marker is given a physical characteristic which enables optical identification thereof along a rotation direction of the substrate for sample analysis, the sample analysis device further comprising:
a light source; and
a photodetector that detects light from the light source which has passed through the substrate for sample analysis when the light is radiated from the light source onto the substrate for sample analysis in rotation, wherein the origin detection circuit determines a position of the marker by detecting the physical characteristic based on a detection result of the photodetector.

13. The sample analysis device according to claim 12, wherein:
the substrate for sample analysis includes, along the rotation direction, a portion having a first transmittance and another portion having a second transmittance different from the first transmittance; and
the marker is the portion having the first transmittance.

14. The sample analysis device according to claim 12, wherein the photodetector is used as a photodetector to optically analyze the liquid in the substrate for sample analysis.

15. The sample analysis device according to claim 13, wherein the first transmittance is generally zero.

16. A sample analysis method using a sample analysis device for transferring and analyzing a liquid in a substrate for sample analysis loaded therein by rotating the substrate for sample analysis, wherein a marker given a predetermined physical characteristic is provided at a predetermined position on the substrate for sample analysis, the sample analysis device comprising:
a brushless motor;
a rotational angle detection circuit that detects a rotational angle of the brushless motor; and
an origin detection circuit that detects a position of the marker by detecting the predetermined physical characteristic and determines the position of the marker to be an origin position, wherein:
the brushless motor includes:
a 2n-pole (n: an integer of 1 or more) rotor; and
a first Hall element and a second Hall element arranged in a positional relationship of an angle α ($0°<α<180°$) from each other with respect to a rotation axis of the rotor, the first Hall element and the second Hall element each outputting a voltage signal in accordance with a magnetic field of the rotor,
the sample analysis method comprising steps of:
receiving the voltage signals output respectively from the first Hall element and the second Hall element;
detecting a phase of the rotor by using values of the voltage signals and information of the angle α;
detecting a predetermined reference angle, by an angle calculation circuit, based on the origin position detected by the origin detection circuit; and
calculating a rotational angle of the rotor, by the angle calculation circuit, calculated from an initial angle of the rotor based on the phase detected in the phase detecting step and the predetermined reference angle,
when the voltage signal of the first Hall element is denoted as H1=A sin ωt and the voltage signal of the second Hall element is denoted as H2=A sin(ωt+α), or
when the voltage signal of the first Hall element is denoted as H1=f(t)A sin ωt and the voltage signal of the second Hall element is denoted as H2=f(t)A sin(ωt+α), and a function f(t) is a noise component which is commonly superimposed on the first Hall element and the second Hall element,
the rotor phase detecting step includes detecting a phase θ of the rotor by calculating:

θ=tan$^{-1}$(H1·sin α)/(H2−H1·cos α), and wherein:
at a first point in time, detecting a first phase of the rotor; and calculating a first rotational angle of the rotor from the initial angle of the rotor based on the first phase and the predetermined reference angle, and further updating the predetermined reference angle to the first phase; and
at a second point in time different from the first point in time, detecting a second phase of the rotor; and calculating a rotational angle of the rotor from the predetermined reference angle based on the first rotational angle, the second phase and the updated predetermined reference angle.

17. A non-transitory computer-readable storage medium storing a computer program for controlling a sample analysis device for transferring and analyzing a liquid in a substrate for sample analysis loaded therein by rotating the substrate for sample analysis, wherein a marker given a predetermined physical characteristic is provided at a predetermined position on the substrate for sample analysis, the sample analysis device comprising:
a brushless motor;
a rotational angle detection circuit that detects a rotational angle of the brushless motor; and
an origin detection circuit that detects a position of the marker by detecting the predetermined physical characteristic and determines the position of the marker to be an origin position, wherein:
the brushless motor includes:
a 2n-pole (n: an integer of 1 or more) rotor; and
a first Hall element and a second Hall element arranged in a positional relationship of an angle α ($0°<α<180°$) from each other with respect to a rotation axis of the rotor, the first Hall element and the second Hall element each outputting a voltage signal in accordance with a magnetic field of the rotor; and
the computer program instructs a computer to execute steps of:
receiving the voltage signals output respectively from the first Hall element and the second Hall element;
detecting a phase of the rotor by using values of the voltage signals and information of the angle α,
when the voltage signal of the first Hall element is denoted as H1=A sin ωt and the voltage signal of the second Hall element is denoted as H2=A sin(ωt+α), or
when the voltage signal of the first Hall element is denoted as H1=f(t)A sin ωt and the voltage signal of the second Hall element is denoted as H2=f(t)A sin(ωt+α), and a function f(t) is a noise component which is commonly superimposed on the first Hall element and the second Hall element,
detecting a phase θ of the rotor by calculating:

θ=tan$^{-1}$(H1·sin α)/(H2−H1·cos α);

detecting a predetermined reference angle, by an angle calculation circuit, based on the origin position detected by the origin detection circuit; and
calculating a rotational angle of the rotor calculated from an initial angle of the rotor based on the phase detected in the phase detecting step and the predetermined reference angle,
wherein:
at a first point in time, detecting a first phase of the rotor; and calculating a first rotational angle of the rotor from the initial angle of the rotor based on the first phase and the predetermined reference angle, and further updating the predetermined reference angle to the first phase; and at a second point in time different from the first point in time, detecting a second phase of the rotor; and calculating a rotational angle of the rotor from the predetermined reference angle based on the first rotational angle, the second phase and the updated predetermined reference angle.

18. A sample analysis device for transferring and analyzing a liquid in a substrate for sample analysis loaded therein by rotating the substrate for sample analysis, wherein:

a marker given a predetermined physical characteristic is provided at a predetermined position on the substrate for sample analysis, the sample analysis device comprising:

a brushless motor that rotates the substrate for sample analysis, the brushless motor including a 2n-pole (n: an integer of 1 or more) rotor and a first Hall element and a second Hall element arranged at an angle α (0°<α<180°) from each other with respect to a rotation axis of the rotor, the first Hall element and the second Hall element each outputting a voltage signal in accordance with a magnetic field of the rotor;

a driver circuit that controls how the brushless motor is driven;

an origin detection circuit that detects a position of the marker by detecting the predetermined physical characteristic and determines the position of the marker to be an origin position;

a rotational angle detection circuit that detects a rotational angle of the brushless motor;

a light source; and a photodetector that detects light from the light source which has passed through the substrate for sample analysis when the light is radiated from the light source onto the substrate for sample analysis in rotation, wherein:

the brushless motor includes:

a 2n-pole (n: an integer of 1 or more) rotor; and a first Hall element and a second Hall element arranged at a positional relationship of an angle α (0°<α<180°) from each other with respect to a rotation axis of the rotor, the first Hall element and the second Hall element each outputting a voltage signal in accordance with a magnitude of a magnetic field of the rotor;

the rotational angle detection circuit includes:

a phase detection circuit that receives the voltage signals output respectively from the first Hall element and the second Hall element and that detects a phase of the rotor by using values of the voltage signals and information of the angle α; and an angle calculation circuit that calculates a rotational angle of the rotor calculated from an initial angle of the rotor based on the phase detected by the phase detection circuit and a predetermined reference angle;

the phase detection circuit detects a phase of the rotor at a point in time when the origin position is detected by the origin detection circuit;

the angle calculation circuit sets, as the predetermined reference angle, a phase of the rotor at the point in time and calculates a rotational angle of the rotor from the predetermined reference angle based on the phase detected by the phase detection circuit and the predetermined reference angle;

the marker is given a physical characteristic which enables optical identification thereof along a rotation direction of the substrate for sample analysis;

the origin detection circuit determines a position of the marker by detecting the physical characteristic based on a detection result of the photodetector; and the photodetector is used as a photodetector to optically analyze the liquid in the substrate for sample analysis.

* * * * *